United States Patent
Mahmoud et al.

(10) Patent No.: US 10,922,567 B2
(45) Date of Patent: Feb. 16, 2021

(54) COGNITIVE STATE BASED VEHICLE MANIPULATION USING NEAR-INFRARED IMAGE PROCESSING

(71) Applicant: Affectiva, Inc., Boston, MA (US)

(72) Inventors: Abdelrahman N. Mahmoud, Somerville, MA (US); Rana el Kaliouby, Milton, MA (US); Seyedmohammad Mavadati, Watertown, MA (US); Panu James Turcot, Pacifica, CA (US)

(73) Assignee: Affectiva, Inc., Boston, MA (US)

( * ) Notice: Subject to any disclaimer, the term of this patent is extended or adjusted under 35 U.S.C. 154(b) by 174 days.

(21) Appl. No.: 16/289,870

(22) Filed: Mar. 1, 2019

(65) Prior Publication Data

US 2019/0197330 A1   Jun. 27, 2019

Related U.S. Application Data

(63) Continuation-in-part of application No. 15/875,644, filed on Jan. 19, 2018, now Pat. No. 10,627,817, (Continued)

(51) Int. Cl.
G06K 9/00         (2006.01)
G08G 1/0967       (2006.01)
(Continued)

(52) U.S. Cl.
CPC ......... *G06K 9/00845* (2013.01); *B60W 40/08* (2013.01); *G06K 9/00288* (2013.01);
(Continued)

(58) Field of Classification Search
USPC .......................................................... 701/36
See application file for complete search history.

(56) References Cited

U.S. PATENT DOCUMENTS 3,034,500 A   5/1962   Backster, Jr.
3,548,806 A   12/1970  Fisher
(Continued)

FOREIGN PATENT DOCUMENTS

JP        08115367       7/1996
KR   10-2005-0021759 A   3/2005
(Continued)

OTHER PUBLICATIONS

Fasel, B. (Aug. 2002). Robust face analysis using convolutional neural networks. In Object recognition supported by user interaction for service robots (vol. 2, pp. 40-43). IEEE.
(Continued)

Primary Examiner — Tyler D Paige
(74) Attorney, Agent, or Firm — Adams Intellex, PLC

(57) ABSTRACT

Cognitive state-based vehicle manipulation uses near-infrared image processing. Images of a vehicle occupant are obtained using imaging devices within a vehicle. The images include facial data of the vehicle occupant. The images include visible light-based images and near-infrared based images. A classifier is trained based on the visible light content of the images to determine cognitive state data for the vehicle occupant. The classifier is modified based on the near-infrared image content. The modified classifier is deployed for analysis of additional images of the vehicle occupant, where the additional images are near-infrared based images. The additional images are analyzed to determine a cognitive state. The vehicle is manipulated based on the cognitive state that was analyzed. The cognitive state is rendered on a display located within the vehicle.

26 Claims, 17 Drawing Sheets

Related U.S. Application Data which is a continuation-in-part of application No. 15/273,765, filed on Sep. 23, 2016, now abandoned, which is a continuation-in-part of application No. 14/796,419, filed on Jul. 10, 2015, now abandoned, which is a continuation-in-part of application No. 14/460,915, filed on Aug. 15, 2014, now abandoned, which is a continuation-in-part of application No. 13/153,745, filed on Jun. 6, 2011, now abandoned.

(60) Provisional application No. 62/679,825, filed on Jun. 3, 2018, provisional application No. 62/637,567, filed on Mar. 2, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | | |
|---|---|---|
| *G08G 1/01* | (2006.01) | |
| *G06N 7/00* | (2006.01) | |
| *H04N 5/00* | (2011.01) | |
| *B60W 40/08* | (2012.01) | |
| *G06N 3/08* | (2006.01) | |
| *G06N 3/04* | (2006.01) | |
| *G06K 9/62* | (2006.01) | |
| *G10L 25/51* | (2013.01) | |
| *G10L 25/78* | (2013.01) | |
| *H04N 5/247* | (2006.01) | |
| *H04N 5/33* | (2006.01) | |
| *G06N 3/00* | (2006.01) | |
| *G06N 20/10* | (2019.01) | |
| *B60R 11/00* | (2006.01) | |
| *B60R 11/02* | (2006.01) | |
| *H04N 7/18* | (2006.01) | |
| *G10L 25/48* | (2013.01) | |

(52) U.S. Cl.
CPC ..... *G06K 9/00315* (2013.01); *G06K 9/00838* (2013.01); *G06K 9/6256* (2013.01); *G06K 9/6273* (2013.01); *G06K 9/6289* (2013.01); *G06N 3/006* (2013.01); *G06N 3/04* (2013.01); *G06N 3/0454* (2013.01); *G06N 3/08* (2013.01); *G06N 3/084* (2013.01); *G06N 7/005* (2013.01); *G06N 20/10* (2019.01); *G08G 1/0112* (2013.01); *G08G 1/0129* (2013.01); *G08G 1/096716* (2013.01); *G08G 1/096725* (2013.01); *G08G 1/096741* (2013.01); *G08G 1/096775* (2013.01); *G10L 25/51* (2013.01); *G10L 25/78* (2013.01); *H04N 5/247* (2013.01); *H04N 5/33* (2013.01); *B60R 11/0247* (2013.01); *B60R 2011/0003* (2013.01); *G10L 25/48* (2013.01); *H04N 7/18* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |

(56) References Cited

U.S. PATENT DOCUMENTS

| | | | |
|---|---|---|---|
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ballet et al. | |
| 6,222,607 B1 | 4/2001 | Szajewski et al. | |
| 6,309,342 B1 | 10/2001 | Blazey et al. | |
| 6,327,580 B1 | 12/2001 | Pierce et al. | |
| 6,349,290 B1 | 2/2002 | Horowitz et al. | |
| 6,351,273 B1 | 2/2002 | Lemelson et al. | |
| 6,437,758 B1 | 8/2002 | Nielsen et al. | |
| 6,443,840 B2 | 9/2002 | Von Kohorn | |
| 6,530,082 B1 | 3/2003 | Del Sesto et al. | |
| 6,577,329 B1 | 6/2003 | Flickner et al. | |
| 6,606,102 B1 | 8/2003 | Odom | |
| 6,629,104 B1 | 9/2003 | Parulski et al. | |
| 6,724,920 B1* | 4/2004 | Berenz | G06K 9/00221 |
| | | | 180/169 |
| 6,792,458 B1 | 9/2004 | Muret et al. | |
| 6,847,376 B2 | 1/2005 | Engeldrum et al. | |
| 6,996,256 B2* | 2/2006 | Pavlidis | A61B 5/015 |
| | | | 382/118 |
| 7,003,135 B2 | 2/2006 | Hsieh et al. | |
| 7,013,478 B1 | 3/2006 | Hendricks et al. | |
| 7,027,621 B1 | 4/2006 | Prokoski | |
| 7,110,570 B1 | 9/2006 | Berenz et al. | |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,319,779 B1 | 1/2008 | Mummareddy et al. | |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,757,171 B1 | 7/2010 | Wong et al. | |
| 7,826,657 B2 | 11/2010 | Zhang et al. | |
| 7,830,570 B2 | 11/2010 | Morita et al. | |
| 7,881,493 B1 | 2/2011 | Edwards et al. | |
| 7,921,036 B1 | 4/2011 | Sharma | |
| 8,010,458 B2 | 8/2011 | Galbreath et al. | |
| 8,022,831 B1 | 9/2011 | Wood-Eyre | |
| 8,219,438 B1 | 7/2012 | Moon et al. | |
| 8,300,891 B2 | 10/2012 | Chen et al. | |
| 8,369,608 B2 | 2/2013 | Gunaratne | |
| 8,401,248 B1 | 3/2013 | Moon et al. | |
| 8,442,638 B2 | 5/2013 | Libbus et al. | |
| 8,522,779 B2 | 9/2013 | Lee et al. | |
| 8,600,120 B2 | 12/2013 | Gonion et al. | |
| 8,640,021 B2 | 1/2014 | Perez et al. | |
| 8,738,523 B1 | 5/2014 | Sanchez et al. | |
| 8,947,217 B2 | 2/2015 | Moussa et al. | |
| 9,460,601 B2 | 10/2016 | Mimar | |
| 9,483,695 B2 | 11/2016 | S. et al. | |
| 9,721,173 B2 | 8/2017 | Xu et al. | |
| 9,734,685 B2 | 8/2017 | Fields et al. | |
| 9,834,221 B2 | 12/2017 | Nilsson | |
| 9,843,777 B2 | 12/2017 | Schofield et al. | |
| 10,627,817 B2* | 4/2020 | Zijderveld | A61B 5/6893 |
| 10,779,761 B2* | 9/2020 | el Kaliouby | G08G 1/096725 |
| 10,796,176 B2* | 10/2020 | el Kaliouby | G08G 1/0129 |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman | |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0060728 A1 | 3/2003 | Mandigo | |
| 2003/0093784 A1 | 5/2003 | Dimitrova et al. | |
| 2003/0182123 A1 | 9/2003 | Mitsuyoshi | |
| 2003/0191682 A1 | 10/2003 | Shepard et al. | |
| 2003/0191816 A1 | 10/2003 | Landress et al. | |
| 2004/0181457 A1 | 9/2004 | Biebesheimer | |
| 2005/0187437 A1 | 8/2005 | Matsugu | |
| 2005/0283055 A1 | 12/2005 | Shirai et al. | |
| 2005/0289582 A1 | 12/2005 | Tavares et al. | |
| 2006/0011399 A1 | 1/2006 | Brockway et al. | |
| 2006/0019224 A1 | 1/2006 | Behar et al. | |
| 2006/0143647 A1 | 6/2006 | Bill | |
| 2006/0149428 A1 | 7/2006 | Kim et al. | |
| 2006/0170945 A1 | 8/2006 | Bill | |
| 2006/0235753 A1 | 10/2006 | Kameyama | |
| 2007/0167689 A1 | 7/2007 | Ramadas et al. | |
| 2007/0173733 A1 | 7/2007 | Le et al. | |
| 2007/0239787 A1 | 10/2007 | Cunningham et al. | |
| 2007/0255831 A1 | 11/2007 | Hayashi et al. | |
| 2007/0265507 A1 | 11/2007 | de Lemos | |
| 2007/0299964 A1 | 12/2007 | Wong et al. | |
| 2008/0059570 A1 | 3/2008 | Bill | |
| 2008/0091512 A1 | 4/2008 | Marci et al. | |
| 2008/0091515 A1 | 4/2008 | Thieberger et al. | |
| 2008/0101660 A1 | 5/2008 | Seo | |
| 2008/0103784 A1 | 5/2008 | Wong et al. | |
| 2008/0184170 A1 | 7/2008 | Periyalwar | |
| 2008/0208015 A1 | 8/2008 | Morris et al. | |
| 2008/0221472 A1 | 9/2008 | Lee et al. | |
| 2008/0287821 A1 | 11/2008 | Jung et al. | |
| 2008/0292151 A1 | 11/2008 | Kurtz et al. | |
| 2008/0309468 A1* | 12/2008 | Greene | G08G 1/165 |
| | | | 340/436 |
| 2009/0002178 A1 | 1/2009 | Guday et al. | |
| 2009/0006206 A1 | 1/2009 | Groe | |
| 2009/0083421 A1 | 3/2009 | Glommen et al. | |
| 2009/0094286 A1 | 4/2009 | Lee et al. | |
| 2009/0112694 A1 | 4/2009 | Jung et al. | |
| 2009/0112810 A1 | 4/2009 | Jung et al. | |
| 2009/0133048 A1 | 5/2009 | Gibbs et al. | |
| 2009/0150919 A1 | 6/2009 | Lee et al. | |
| 2009/0156907 A1 | 6/2009 | Jung et al. | |
| 2009/0164132 A1 | 6/2009 | Jung et al. | |
| 2009/0193344 A1 | 7/2009 | Smyers | |
| 2009/0209829 A1 | 8/2009 | Yanagidaira et al. | |
| 2009/0210290 A1 | 8/2009 | Elliott et al. | |
| 2009/0217315 A1 | 8/2009 | Malik et al. | |
| 2009/0259518 A1 | 10/2009 | Harvey | |
| 2009/0270170 A1 | 10/2009 | Patton | |
| 2009/0271417 A1 | 10/2009 | Toebes et al. | |
| 2009/0285456 A1* | 11/2009 | Moon | G06K 9/00335 |
| | | | 382/118 |
| 2009/0299840 A1 | 12/2009 | Smith | |
| 2010/0070523 A1 | 3/2010 | Delgo et al. | |
| 2010/0090839 A1* | 4/2010 | Omi | G06K 9/00228 |
| | | | 340/575 |
| 2010/0099955 A1 | 4/2010 | Thomas et al. | |
| 2010/0134302 A1 | 6/2010 | Ahn et al. | |
| 2010/0191156 A1* | 7/2010 | Sakamoto | A61B 5/165 |
| | | | 600/595 |
| 2010/0266213 A1 | 10/2010 | Hill | |

(56) References Cited

U.S. PATENT DOCUMENTS

| | | |
|---|---|---|
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0109452 A1 | 5/2012 | Autran et al. |
| 2012/0324491 A1 | 12/2012 | Bathiche et al. |
| 2013/0023337 A1 | 1/2013 | Bowers et al. |
| 2013/0116587 A1 | 5/2013 | Sornmo et al. |
| 2013/0197409 A1 | 8/2013 | Baxter et al. |
| 2013/0204455 A1 | 8/2013 | Chia et al. |
| 2014/0171752 A1 | 6/2014 | Park et al. |
| 2014/0172910 A1 | 6/2014 | Jung et al. |
| 2014/0218187 A1 | 8/2014 | Chun et al. |
| 2014/0309813 A1* | 10/2014 | Ricci ................. H04W 4/60 701/2 |
| 2015/0258995 A1 | 9/2015 | Essers et al. |
| 2016/0037064 A1 | 2/2016 | Stein et al. |
| 2016/0104486 A1 | 4/2016 | Penilla et al. |
| 2016/0185354 A1* | 6/2016 | Lisseman ............ B60W 10/20 701/36 |
| 2016/0191859 A1* | 6/2016 | Lisseman ............ B60K 35/00 348/148 |
| 2017/0003784 A1 | 1/2017 | Garg et al. |
| 2017/0237946 A1 | 8/2017 | Schofield et al. |
| 2017/0297490 A1 | 10/2017 | Lynam et al. |
| 2017/0367635 A1 | 12/2017 | Hur et al. |
| 2020/0239002 A1* | 7/2020 | Sobhany ............ G06K 9/6267 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

Matsugu, M., Mori, K., Mitari, Y., & Kaneda, Y. (2003). Subject independent facial expression recognition with robust face detection using a convolutional neural network. Neural Networks, 16(5-6), 555-559.

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

* cited by examiner

COGNITIVE STATE BASED VEHICLE MANIPULATION USING NEAR-INFRARED IMAGE PROCESSING

RELATED APPLICATIONS

This application claims the benefit of U.S. provisional patent applications "Cognitive State Based Vehicle Manipulation Using Near Infrared Image Processing" Ser. No. 62/637,567, filed Mar. 2, 2018, and "Vehicle Manipulation Using Cognitive State Engineering" Ser. No. 62/679,825, filed Jun. 3, 2018.

This application is also a continuation-in-part of U.S. patent application "Vehicle Manipulation using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017.

The patent application "Vehicle Manipulation using Occupant Image Analysis" Ser. No. 15/875,644, filed Jan. 19, 2018, is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF ART

This application relates generally to image-based analysis and more particularly to cognitive-based vehicle manipulation using near-infrared image processing.

BACKGROUND

A wide variety cognitive states, moods, and emotions are experienced while people travel because transportation routinely presents travelers with situations that can be physically, mentally, and emotionally challenging. Travel situations include being stuck in gridlocked traffic, waiting in endless security check lines that appear never to move, and many others. Despite these situations, the individuals travel from one location to another for financial reasons such as commuting to and from work or school; for personal reasons such as vacation, recovery, relaxation, or adventure; or for exercise, to name only a few. For other individuals, travel is undesirable. These unwilling travelers may be fleeing from war, famine, natural or environmental disasters, or may be victims of economic displacement. Transportation modes include ground transportation, water transportation, and air transportation. The transportation modes are chosen by travelers based on convenience, availability, and/or cost. Transportation modes further depend on the purpose of the travel such as getting across town or hauling goods. Other modes of transportation, such as space transportation, may be available in the near future.

Whichever transportation mode is chosen, people spend a substantial amount of time traveling. Travel related activities including getting to, waiting for, traveling in, or parking the vehicle; waiting in security lines to get on the vehicle; among many others, all consume time. Traveling is time consuming at its best, and loathsome, frustrating, irritating, and stressful at its worst. Some travelers use public transportation networks, such as buses, trains, and airplanes; ride-sharing services such as Uber™ and Lyft™; personal vehicles; and car sharing services such as Zipcar™; to travel among various destinations. Travel times include daily commutes to and from the office, taking the kids to school, soccer practice and piano lessons, taking the pets to the veterinary, shopping, running errands, traveling for business or vacation, and the many other common activities that require transportation. Individuals meet their transportation needs by using a variety of vehicles. The choice of vehicles available most often depends on where people live. The vehicles can include cars and motorcycles; buses, trains and subways; ride and ride sharing services; and even unmotorized vehicles such as bicycles, skateboards, or scooters. The time spent on travel is time lost from productive or meaningful activities such as work, study, artistic pursuits, being with family or friends, and so on. Rush hour traffic, accidents, and poorly maintained roads greatly complicate and interfere with vehicle transportation. The difficulties of transportation are further exacerbated by operating an unfamiliar vehicle, traveling in an unfamiliar city, and even in some situations having to remember to operate a vehicle on the opposite side of the road. Catastrophic consequences can result from failure to remain alert to these transportation realities. Irritated or belligerent vehicle operators can experience road rage and other antisocial behaviors, while bored, impaired, sleepy, distracted, or inattentive drivers can cause vehicular accidents resulting in injury to themselves or other vehicle occupants, pedestrians, bicyclists, or animals, and damage to property.

Transportation systems are complex. Transportation in general, and specifically urban transportation, present labyrinthine and difficult design, financial, and management problems, any of which can directly impact travelers. Overly congested highways and surface roads, and chronically insufficient parking, each directly influence the cognitive or mental states, moods, and emotions of travelers. The congested roadways cause significantly longer and more dangerous commutes, while the lack of available parking increases the amount of time wasted looking for a place to leave a vehicle safely. Public transportation, if at all available to the traveler at her particular location, presents challenges of its own. The challenges include overfilled buses, trains, and subways during commuting hours; underused routes due to poor planning or a general lack of interest, and other factors. The increased use of bicycles or scooters through sharing services presents other, further challenges. Challenging or dangerous situations arise when vehicles, bicycles, or scooters share overfilled roadways that were not originally or mindfully designed for multi-use scenarios.

Although vehicle operators and occupants may not be directly involved in the management and financing of transportation systems, those travelers directly suffer from and experience the frustration and annoyance of using the transportation systems, all while carrying the tax burden of paying to construct, maintain, operate, and upgrade those systems.

SUMMARY

Vehicular manipulation in disclosed techniques uses image-based analysis of a vehicle occupant. The vehicle to be manipulated can be an autonomous vehicle, a semi-autonomous vehicle, and so on. An in-vehicle imaging device is used to collect images of a vehicle occupant, where the images include facial data. The vehicle can be a first vehicle, a second vehicle, a third vehicle, a public transportation vehicle, etc. The images can include visible light images and near-infrared (NIR) images. Other in-vehicle sensors can include a microphone for collecting audio data or voice data, and other sensors to collect physiological data. A classifier is trained based on the light content of the images of the vehicle occupant to determine cognitive state data for the vehicle occupant. The light can include visible light, near-infrared light, and so on. The classifier can be modified. The modifying of the classifier can be based on the near-infrared content from the images or on the visible light content from the images. The classifier is deployed for analysis of additional images of a vehicle occupant. The classifier that is deployed can be a trained classifier, a modified classifier, etc. The additional images can include NIR images or visible light images. The vehicle occupant can be the operator or driver of the vehicle, a passenger in the vehicle, and so on. The additional images are analyzed to determine a cognitive state. The vehicle is manipulated based on the cognitive state that was analyzed.

In embodiments, a computer-implemented method for image-based analysis comprises: obtaining a plurality of images of a vehicle occupant using one or more imaging devices within a vehicle, wherein the plurality of images includes facial data of the vehicle occupant and wherein the plurality of images includes visible light-based images and near-infrared based images; training, using a first computing device, a classifier, based on the visible light content of the one or more images to determine cognitive state data for the vehicle occupant; modifying the classifier based on near-infrared content from the plurality of images; deploying, on a second computing device, the classifier that was modified, for analysis of a plurality of additional images of a vehicle occupant that is obtained, wherein the plurality of additional images comprises near-infrared based images; analyzing, using the second computing device, the plurality of additional images to determine a cognitive state; and manipulating the vehicle, based on the cognitive state that was analyzed. In some embodiments, the method includes obtaining audio information from the occupant of the vehicle and augmenting the analyzing based on the audio information. The occupant can be a driver or operator of the vehicle or can be a passenger within the vehicle. The vehicle can be an autonomous vehicle or a semi-autonomous vehicle. In embodiments, the method includes rendering the cognitive state on a display located within the vehicle. The rendering the information can include showing the information on an in-dashboard display, an in-vehicle display, a heads-up display, an electronic device associated with the vehicle occupant, etc. In other embodiments, the information that was updated includes road ratings for one or more segments of a vehicle travel route. The aggregated cognitive state data for one or more segments of the vehicle travel route can include a vehicle route mood map.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
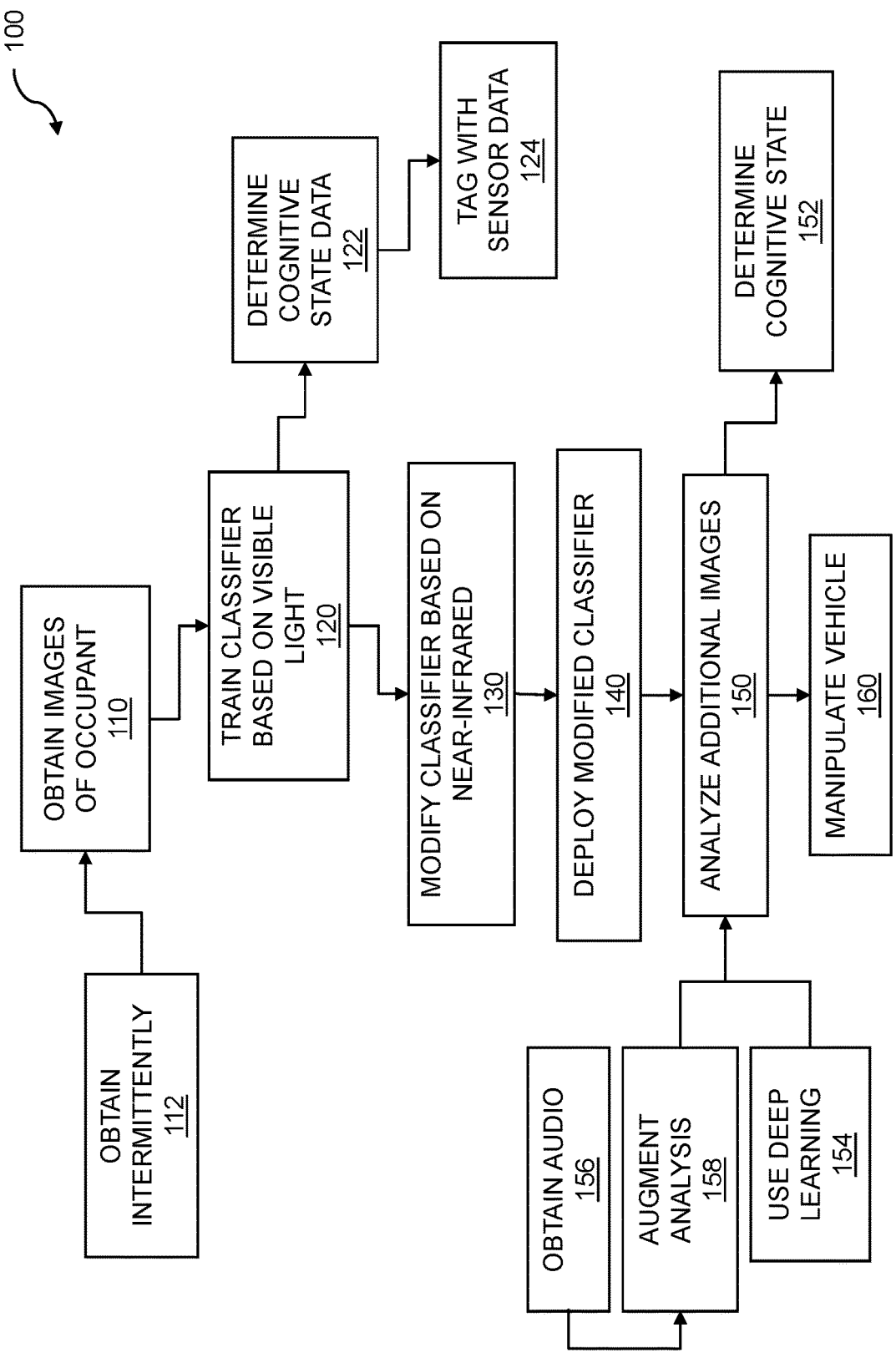
FIG. 1 is a flow diagram for cognitive state based vehicle manipulation.

Many individuals spend hundreds of hours or more per year traveling in vehicles. The vehicles that are typically used for travel include public, private, or commercial vehicles, such as buses, trains, airplanes, automobiles, ride share vehicles, and so on. The hours that individuals are in vehicles are spent commuting to and from work, running errands, meeting appointments, traveling, etc. An individual who is traveling within or atop a vehicle can experience a wide range of cognitive states. The individual's cognitive states can be determined by analyzing cognitive state data that can be collected from the individual. The cognitive state data can include image data, facial data, audio data, voice data, speech data, non-speech vocalizations, physiological data, etc. The analysis of the cognitive state data for the vehicle occupant can be used to manipulate the vehicle. The vehicle manipulation can be provided to authorize a person to access or operate a vehicle, to configure the vehicle based on preferences of a vehicle occupant, to control or operate an autonomous or semi-autonomous vehicle, and so on. The vehicle manipulation can include routing a vehicle along a vehicle travel route that is best suited to the cognitive state of the vehicle occupant. The vehicle travel route can be manipulated based on a route ranking of "low stress", "beautiful", "happy", and so on. Vehicle occupant cognitive states including moods can be determined from a vehicle route mood map.

Other determinations can be made based on vehicle occupant's cognitive state. The determinations can include whether the occupant is in a fit cognitive state to operate the vehicle safely (e.g. not impaired); should take a break from operating or traveling in the vehicle during long trips; should seek an alternative travel route due to weather, accident, or construction, and so on. The determinations of cognitive states and the vehicle manipulations directly benefit vehicle operator or passenger convenience and comfort, improve road safety, enhance transportation experiences, etc. Further, collecting cognitive state data enables manipulation of vehicle operating characteristics and vehicle environmental experiences for the operators and passengers. The vehicle in which the vehicle occupant or occupants are traveling can be an autonomous vehicle, a semi-autonomous vehicle, etc. The benefits of manipulating an autonomous vehicle or a semi-autonomous vehicle range from reducing the time required to configure a vehicle to an individual to verifying that the individual is in a cognitive state capable of operating the vehicle, is permitted to operate the vehicle, etc. The enhanced transportation experience for the individual includes autonomous operation, security, or comfort. The road safety improvements derived from manipulating the vehicle on behalf of the individual include safer vehicle operations when navigating in foreign surroundings or operating an unfamiliar vehicle, and preventing a sleepy, impaired, or inattentive individual from operating the vehicle.

In the disclosed techniques, cognitive state based vehicle manipulation, where the vehicles can include semi-autonomous vehicles or autonomous vehicles, uses near-infrared image processing. Vehicle manipulation can be performed for a variety of purposes including assisting an occupant of the vehicle, permitting access to a vehicle, configuring the vehicle based on preferences of the vehicle occupant, and so on. The vehicle manipulation can also include choosing routes for the vehicle based on a vehicle route mood map, improving comfort of the occupant, reducing stress and other negative cognitive states, and so on. The vehicle manipulation uses image-based analysis. Images of a vehicle occupant are obtained using one or more imaging devices within a vehicle. The imaging devices can include cameras, where the cameras can include a video camera, a still camera, a camera array, a plenoptic camera, a web-enabled camera, a visible light camera, a near-infrared (NIR) camera, a heat camera, and so on. The obtained images include facial data of the vehicle occupant. The images further include visible light-based images and near-infrared based images. A classifier is trained using a first computing device. The first computing device can include an on-board computer, an electronic device used by the vehicle occupant, a server located beyond the vehicle, etc. The classifier that is trained is based on the visible light content or near-infrared content of the one or more images to determine cognitive state data for the vehicle occupant. The cognitive states can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The classifier can be modified based on near-infrared content or visible light content from the plurality of images. The classifier or the classifier that was modified is deployed on a second computing device. The second computing device can be the same device as the first computing device. The second computing device can include an on-board computer, an electronic device used by the vehicle occupant, a server located beyond the vehicle, etc. The classifier or the modified classifier is deployed for analysis of additional images obtained of a vehicle occupant. The additional images can include near-infrared based images or visible light images. The additional images are analyzed to determine a cognitive state. The vehicle is manipulated based on the cognitive state that was analyzed. The cognitive state can be rendered on a display located within the vehicle. The cognitive state can be transmitted to a third computing device, where the third computing device is external to the vehicle.

FIG. 1 is a flow diagram for cognitive state based vehicle manipulation. The cognitive state based vehicle manipulation uses image-based analysis of near-infrared images. Images including facial data contain visible light images or near-infrared images of a vehicle occupant. A classifier is trained or modified to determine cognitive state data for the vehicle occupant. The classifier is deployed for analysis of additional images. The additional images are analyzed for a cognitive state, and the vehicle is manipulated based on the cognitive state. In some embodiments, vehicle manipulation can simply include observing or monitoring an occupant or driver within a vehicle.

The flow 100 includes obtaining a plurality of images of a vehicle occupant 110 using one or more imaging devices within a vehicle, where the plurality of images includes facial data of the vehicle occupant and where the plurality of images includes visible light-based images and near-infrared based images. The one or more imaging devices can include any of a variety of cameras or other image capture devices suitable for image-based analysis. A camera can include a webcam, a video camera, a still camera, a thermal imager, a near infrared (NIR) camera, a CCD device, a phone camera, a three-dimensional camera, a depth camera, a light field camera, multiple webcams used to show different views of a person, or any image capture device. A camera or image capture device can capture light of various wavelengths. In embodiments, a wavelength of the near infrared light can be less than 950 nm. Other types of data pertaining to a vehicle occupant can be collected. In some embodiments, audio data is collected in place of images or in addition to images to augment the cognitive state data contained therein. In embodiments, the vehicle occupant can be the driver of the vehicle, the operator of the vehicle, a passenger of the vehicle, etc. The vehicle can be an automobile, a bus, a van, a truck, a train, an airplane, a ship, etc. Embodiments include intermittent obtaining of images 112 that include facial data.

The flow 100 includes using a first computing device to train a classifier, based on the visible light content 120 of the one or more images to determine cognitive state data 122 for the vehicle occupant. The first computing device can include a computing device coupled to the vehicle; an electronic device, such as a smartphone, a personal digital assistant (PDA), a tablet computer, a laptop computer, etc., associated with the vehicle occupant; a local server, and so on. The classifier can be trained using other light content of the images such as near-infrared content. The cognitive state data can include image data, facial data, audio data, voice data, and so on. Embodiments further include tagging the cognitive state data with sensor data 124. The sensor data can be related to the vehicle occupant and can include physiological data such as heart rate, heart rate variability, respiration rate, skin conductivity, and so on. In embodiments, the sensor data can include one or more of vehicle temperature, outside temperature, time of day, level of daylight, weather conditions, headlight activation, windshield wiper activation, entertainment center selection, or entertainment center volume.

The flow 100 includes modifying the classifier 130 based on near-infrared content from the plurality of images. The training and the modifying of the classifier can be based on a variety of image content types. While in some embodiments, the classifier is trained with visible light content and modified with near-infrared content, in other embodiments, the classifier is trained with either visible light content or near-infrared content. The modifying the classifier can include modifying with near-infrared content or visible light content. The flow 100 includes deploying, on a second computing device, the classifier that was modified 140 for analysis of a plurality of additional images of a vehicle occupant that is obtained, wherein the plurality of additional images includes near-infrared based images. The second computing device can be located within the vehicle, beyond the vehicle, and so on. The second computing device can be the same computing device as the first computing device. The second computing device can include an electronic device associated with the vehicle occupant. The second computing device can include a local server, a remote server, a cloud-based server, and the like. The additional images can be of the same vehicle occupant as the first images or can be of a different vehicle occupant. The additional images can include near-infrared based images, as stated, or can include visible or other light-based images. The additional images can include facial data.

The flow 100 includes analyzing, using the second computing device, the plurality of additional images 150 to determine a cognitive state 152. The cognitive state can be based on the analysis of cognitive state data. In embodiments, the cognitive state data that was analyzed can be based on intermittent obtaining of images, additional images, etc., that include facial data. The cognitive state can be based on the cognitive state data of a vehicle operator or driver, a vehicle passenger, and so on. A cognitive state can include a mental state, an emotional state, a mood, and the like. In embodiments, the cognitive state includes drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. In embodiments, the analyzing can be performed using deep learning 154. The deep learning can be based on a convolutional neural network (CNN). The convolutional neural network can include input layers, hidden layers, bottleneck layers, output layers, and so on. Weights for the various layers of the CNN can be learned and adjusted based on the cognitive state data.

In embodiments, the flow 100 includes obtaining audio information 156 from the vehicle occupant. The audio information can be obtained using a microphone, an audio transducer, an audio interface, and so on. The audio information can include the audio information from the vehicle occupant as well as other audio signals such as ambient vehicle audio, road audio, construction audio, weather audio, etc. The audio information can include speech, where the speech can be generated by the vehicle occupant. The audio can include non-speech vocalizations. The non-speech vocalizations can be generated by the vehicle occupant, where the non-speech vocalizations can include grunts, yelps, squeals, snoring, sighs, laughter, filled pauses, unfilled pauses, or yawns. The flow 100 includes augmenting the analyzing 158 based on the audio information. The augmenting can include determining a co-occurrence of video and audio events. A co-occurrence can include a yawn event such as a facial image event with a hand of a vehicle occupant covering her or his mouth and an audio event of a yawn.

The flow 100 includes manipulating the vehicle 160, based on the cognitive state that was analyzed. The vehicle that is manipulated can include an autonomous vehicle, a semi-autonomous vehicle, and so on. The vehicle can include the first vehicle or another vehicle. The manipulating the vehicle can include a variety of operations such as a locking out operation of the vehicle to prevent unauthorized use or to prevent an impaired driver from operating the vehicle. The manipulating the vehicle can include making recommendations to the vehicle operator such as taking a break, seeking an alternate route, and the like. The manipulating the vehicle can include brake activation, throttle control, steering control, vehicle route navigation, etc. The manipulating the vehicle can be based on convenience, needs, preferences, and so on, of a vehicle operator or vehicle passenger. Such manipulation of the vehicle can include adjusting vehicle seats, where the adjusting can include moving the seat up, down, forward or backward; adjusting seat tilt; adjusting seat temperature, etc. The manipulating the vehicle can include adjusting the climate within the vehicle. The climate within the vehicle can be controlled based on the occupant of the vehicle, time of day, season of year (e.g. heat or air conditioning), and so on. The manipulating the vehicle can include audio stimuli such as alerts, warnings, signals, tones, and so on. The audio stimuli can be manipulated based on a cognitive state profile of the occupant of the vehicle. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
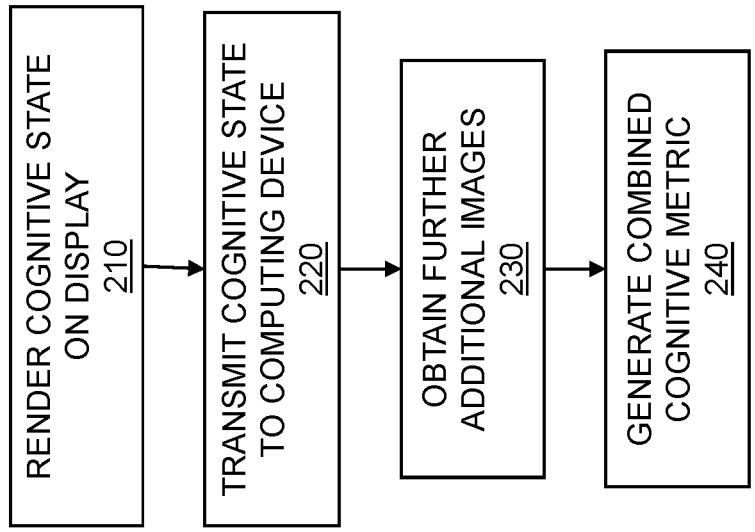
FIG. 2 is a flow diagram for generating a combined cognitive metric.

FIG. 2 is a flow diagram for generating a combined cognitive metric. A combined cognitive metric can be generated for one or more occupants of one or more vehicles. The combined cognitive metric can include a cognitive state, a mental state, an emotional state, a mood, and so on. The combined cognitive metric can be used for cognitive state based vehicle manipulation, where the vehicle manipulation uses near-infrared image processing. Images of a vehicle occupant are obtained using imaging devices within a vehicle. The images can include visible light images or near-infrared images, where the images of any type include facial data. A classifier is trained or modified using the visible light image content or the near-infrared image content. The classifier is deployed for analysis of additional images including near-infrared based images. The additional images are analyzed to determine a cognitive state, and the vehicle is manipulated based on the mental state.

The flow 200 includes rendering the cognitive state on a display 210 located within the vehicle. The display located within the vehicle can include an in-dashboard display, a dashboard-mounted display, a heads-up display, and so on. The display can be coupled to an electronic device associated with the vehicle occupant. The electronic device can include a smartphone, a PDA, a tablet, a laptop computer, a wearable computer such as a smartwatch or smart glasses, and the like. The flow 200 includes transmitting the cognitive state to a third computing device 220, wherein the third computing device is external to the vehicle. A computing device, such as the third computing device, can include a computer, a local server, a remote server, a cloud-based server, a mesh server, and the like. The computing device can be located adjacent to a vehicle travel route. The computing device, including the third computing device, can be accessible using a network including a wireless computer network, a wireless telephone network such as a cellular network, the Internet, and so on. The network can include a Wi-Fi™ network, a Bluetooth™ network, etc.

The flow 200 includes obtaining further additional images 230 of one or more additional occupants of the vehicle, where the further additional images comprise near-infrared based images. The additional occupants of the vehicle can include the operator or driver of the vehicle, passengers within the vehicle, and so on. The further additional images can include multiple angle views of the additional occupants of the vehicle. The further additional images can be analyzed to determine one or more cognitive states of the additional vehicle occupants. Embodiments include obtaining one or more additional images of one or more additional occupants of one or more additional vehicles. The additional occupants can be located in vehicles that are adjacent to the first vehicle from which images of occupants were collected or in vehicles that are remote from the first vehicle. The additional occupants can have cognitive state data that is similar to or different from that of the occupant of the first vehicle.

The flow 200 includes generating a combined cognitive metric 240 for the vehicle occupant and the one or more additional occupants. The combined cognitive metric can be used to determine an intensity, a duration, a decay, and so on, of the cognitive states, mental states, emotional states, moods, etc., of the occupants of the vehicle. In embodiments, the one or more further additional images are used to determine aggregated cognitive state data for one or more segments of the vehicle travel route. The aggregated cognitive state data can be used to determine whether a travel route, for example, should be updated based on the aggregated cognitive state. In embodiments, the aggregated cognitive state data for one or more segments of the vehicle travel route can include a vehicle route mood map. The vehicle route mood map can be used to show whether the one or more segments of the vehicle travel route make the vehicle occupants, happy, sad, angry, stressed, etc. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
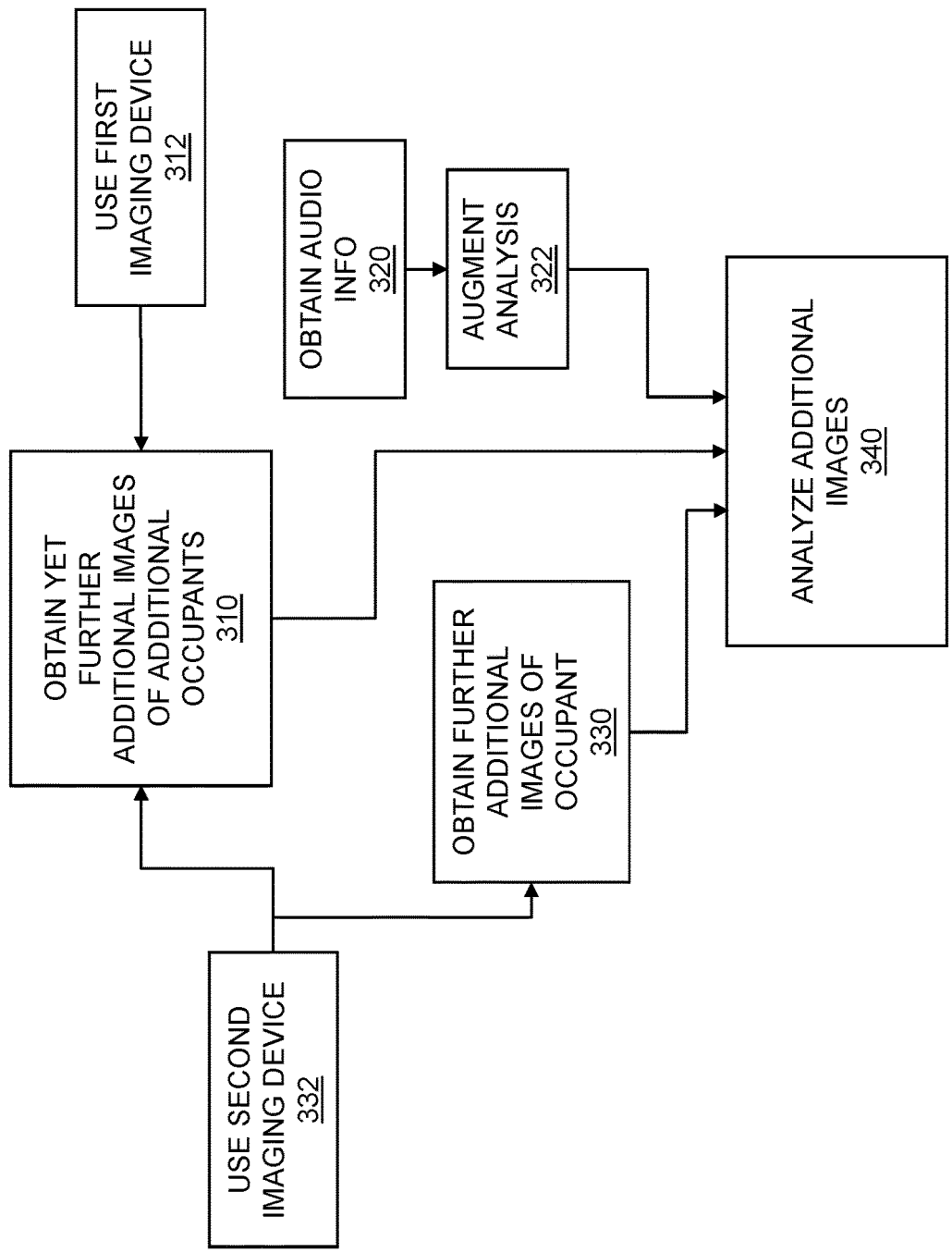
FIG. 3 is a flow diagram for obtaining further images and audio.

FIG. 3 is a flow diagram for obtaining further images and audio. The obtaining further images and audio of a vehicle occupant can support or enhance cognitive state based vehicle manipulation using near-infrared image processing. The further images can include visible light images or near-infrared images. The vehicle occupant can include a driver or operator of the vehicle, a passenger of the vehicle, and so on. The images, including facial data, are obtained using an imaging device within the vehicle. A classifier is trained or modified based on visible light image content or near-infrared image content, and the classifier is deployed for analysis of additional images. The analysis determines a cognitive state, and the vehicle is manipulated based on the cognitive state.

The flow 300 includes obtaining yet further additional images of one or more additional occupants 310 of one or more additional vehicles, where the yet further additional images include near-infrared based images. The further additional images can include visible light images. The yet further additional images can be obtained using a first imaging device 312. The imaging device can be located within a first vehicle, within an additional vehicle, and so on. In other embodiments, the yet further additional images can be obtained using a second imaging device 332. The additional occupants of a given vehicle can be an operator of the vehicle, a passenger of the vehicle, and so on. The additional vehicles can be vehicles similar to a first vehicle, such as substantially similar vehicles from a fleet of vehicles. The additional vehicles can be other vehicles located adjacent to or nearby the first vehicle, such as additional vehicles in traffic. The yet further additional images can be analyzed using a classifier for a variety of purposes. In embodiments, the yet further additional images can be used to determine aggregated cognitive state data for one or more segments of a vehicle travel route. The aggregated cognitive state data can be determined for an occupant of the first vehicle, other occupants of the first vehicle, occupants of the additional vehicles, etc. The aggregated cognitive state can be used to determine an aggregated mental state, an aggregated emotional state, an aggregated mood, and so on. An aggregated cognitive state of frustration, for example, can be determined for drivers of vehicles stuck in traffic. In embodiments, the aggregated cognitive state data for one or more segments of the vehicle travel route can include a vehicle route mood map. Based on a vehicle occupant mood, an aggregated mood across multiple occupants of one or more vehicles, etc., a mood can be assigned to segments of a vehicle travel route. The mood map can show route segments in which vehicle operators or vehicle passengers are anxious, frustrated, angry, and so on. The mood map can include displaying icons, emojis, animations, cartoons, and the like.

The flow 300 includes obtaining audio information 320 from the vehicle occupant and augmenting 322 the analyzing based on the audio information. The audio information can be obtained using a microphone, and audio transducer, an audio interface, and so on. The audio information can include vehicle cabin audio signals and audio signals external to a vehicle such as sounds from a road, traffic, construction, weather, etc. The audio information can include audio signals generated by an occupant of a vehicle. In embodiments, the audio information can include speech. The occupant of the vehicle may be speaking to another occupant such as a passenger, arguing with the radio, and so on. In other embodiments, the audio information can include non-speech vocalizations. The non-speech vocalizations can include other sounds or vocalizations that can be generated by the vehicle occupant. In embodiments, the non-speech vocalizations can include grunts, yelps, squeals, snoring, sighs, laughter, filled pauses, unfilled pauses, or yawns. The obtained audio information can be used for other purposes, such as performing voice recognition on a vehicle occupant, determining a cognitive state such as drowsiness accompanying detected yawns, etc.

The flow 300 includes obtaining one or more further additional images of the vehicle occupant 330 using a second imaging device 332. The further additional images can include different views of the vehicle occupant, intermittent views of the vehicle occupant, and so on. The further additional images can include differing image contents, such as visible light images, near-infrared images, etc. Embodiments further include obtaining one or more further additional images of one or more additional vehicle occupants using the first imaging device. The additional vehicle occupants can be an operator of the vehicle, a passenger of the vehicle, and so on. The first imaging device can include a visible light camera, a near-infrared camera, and the like. Other embodiments include obtaining one or more further additional images of one or more additional vehicle occupants using at least a second imaging device. The second imaging device can be a visible light camera, a near-infrared camera, or another image capture device. The further additional images, obtained using one or more imaging devices, can be used for a variety of techniques. In embodiments the one or more images can be used to perform facial recognition. The facial recognition can be used to allow access to a vehicle, to identify a vehicle operator, to configure a vehicle for an individual occupant, etc. In embodiments, the facial recognition is used to generate vehicle seating maps. The vehicle seating maps can be used for identifying occupants, configuring the vehicle to the preferences of the occupants, determining a composite cognitive state for vehicle occupants, etc. The flow 300 includes analyzing additional images 340. The additional images can include visible light images, near-infrared images, and so on. The additional images can include facial data of one or more occupants of one or more vehicles. The analyzing can include analysis of audio data collected from the one or more occupants of the one or more vehicles. Various steps in the flow 300 may be changed in order, repeated, omitted, or the like without departing from the disclosed concepts. Various embodiments of the flow 300 can be included in a computer program product embodied in a non-transitory computer readable medium that includes code executable by one or more processors.

Figure 4:
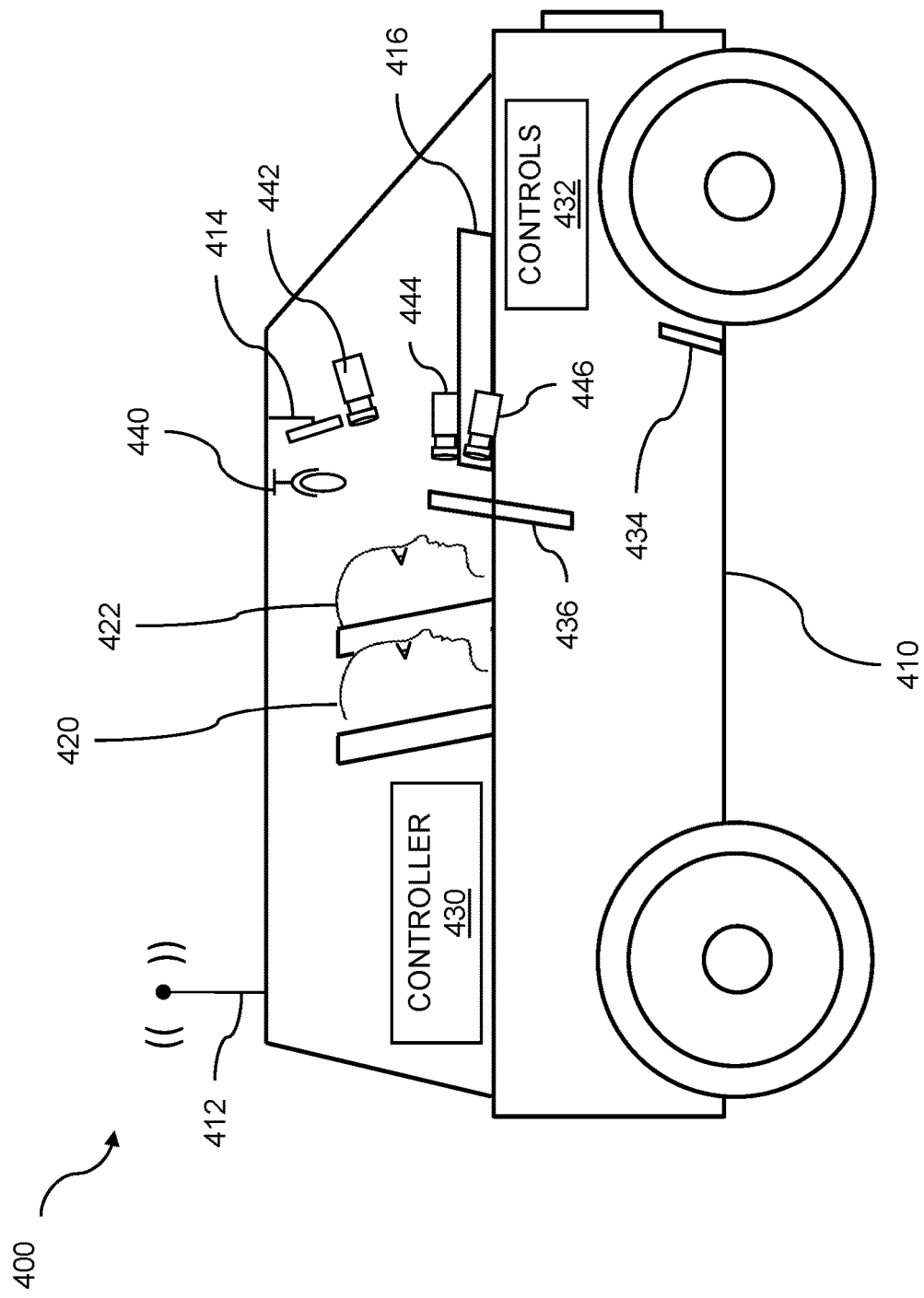
FIG. 4 is a system diagram for an interior of a vehicle.

FIG. 4 is a system diagram for an interior of a vehicle 400. Cognitive state based vehicle manipulation can include near-infrared image processing. Images of a vehicle occupant, including visible light based images and near-infrared based images, are obtained using an imaging device within a vehicle. The images include facial data. A classifier is trained or modified and deployed for analysis of additional images including near-infrared images. The additional images are analyzed to determine a cognitive state, and the vehicle is manipulated based on the cognitive state. One or more occupants of a vehicle 410, such as occupants 420 and 422, can be observed using a microphone 440, one or more cameras 442, 444, or 446, and other audio and image capture techniques. The image data can include video data. The video data and the audio data can include cognitive state data, where the cognitive state data can include facial data, voice data, physiological data, and the like. The occupant can be a driver 422 of the vehicle 410, a passenger 420 within the vehicle, and so on.

The cameras or imaging devices that can be used to obtain images including facial data from the occupants of the vehicle 410 can be positioned to capture the face of the vehicle operator, the face of a vehicle passenger, multiple views of the faces of occupants of the vehicle, and so on. The cameras can be located near a rear-view mirror 414 such as camera 442, positioned near or on a dashboard 416 such as camera 444, positioned within the dashboard such as camera 446, and so on. The microphone or audio capture device 440 can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 410 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 410 can include standard controls such as a steering wheel 436, a throttle control (not shown), a brake 434, and so on. The interior of the vehicle can include other controls 432 such as controls for seats, mirrors, climate controls, audio systems, etc. The controls 432 of the vehicle 410 can be controlled by a controller 430. The controller 430 can control the vehicle 410 in various manners such as autonomously, semi-autonomously, assertively to a vehicle occupant 420 or 422, etc. In embodiments, the controller provides vehicle control or manipulation techniques, assistance, etc. The controller 430 can receive instructions via an antenna 412 or using other wireless techniques. The controller 430 can be preprogrammed to cause the vehicle to follow a specific route. The specific route that the vehicle is programmed to follow can be based on the cognitive state of the vehicle occupant. The specific route can be chosen based on lowest stress, least traffic, most scenic view, shortest distance, and so on.

Figure 5:
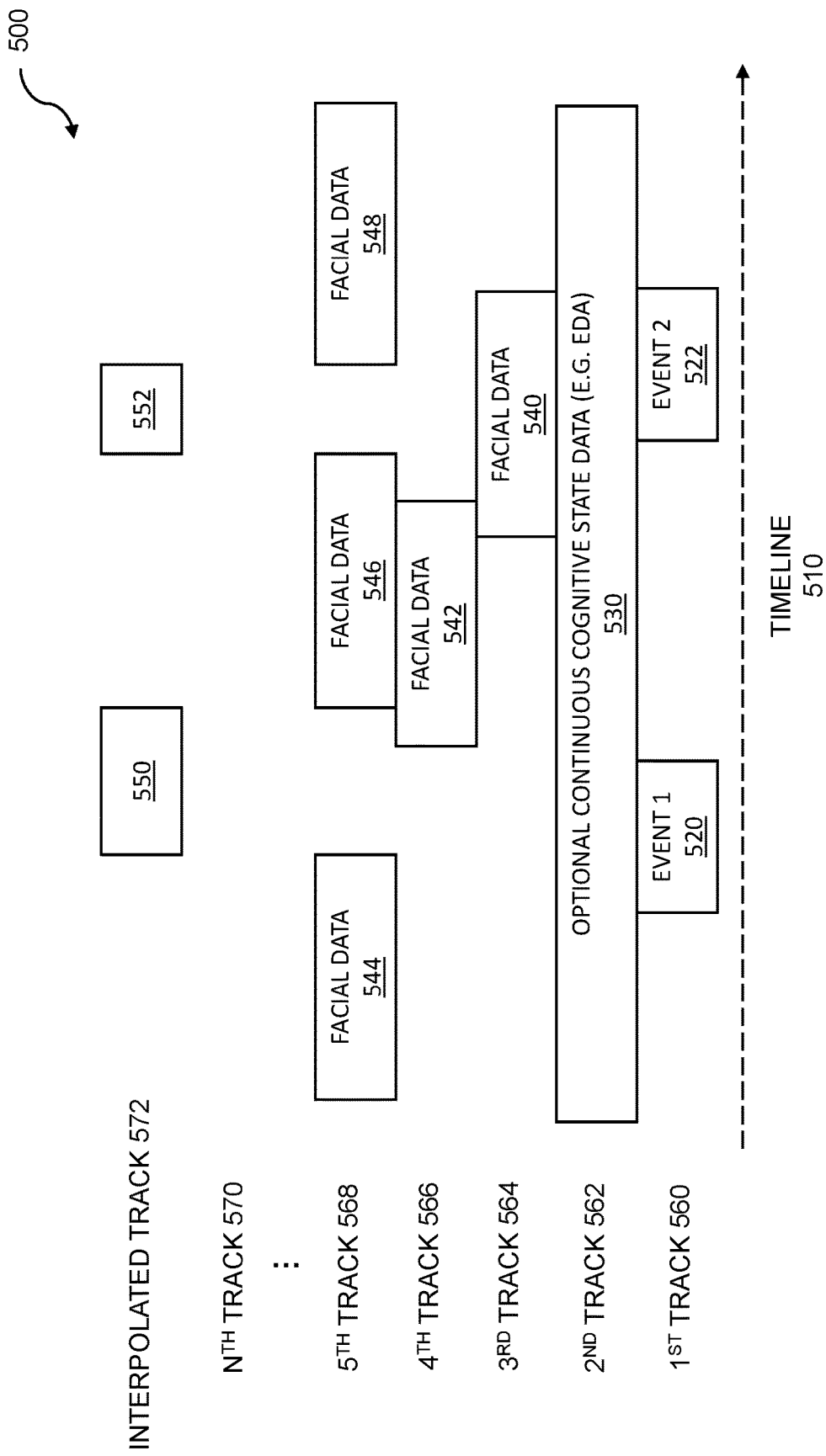
FIG. 5 is a timeline with information tracks relating to cognitive states.

FIG. 5 is a timeline with information tracks relating to cognitive states. A timeline can show one or more cognitive states that can be experienced by a vehicle occupant. The vehicle occupant can be an operator of the vehicle, a passenger of the vehicle, and so on. The timeline can be based on vehicular cognitive data collection using multiple devices. Images of a vehicle occupant are obtained using one or more in-vehicle imaging devices. Visible light content of the images or near-infrared content of the images is used to train or modify a classifier. The classifier is deployed for analysis of additional images that include near-infrared images. The additional images are analyzed to determine a cognitive state. The vehicle is manipulated based on the cognitive state.

The timeline 510 with information tracks 500 relates to various cognitive states. A first track 560 shows events that, in embodiments, are related to use of a computer by the individual. A first event 520 can indicate an action that the individual took (such as launching an application); an action initiated by the computer (such as the presentation of a dialog box); an external event (such as a new global positioning system (GPS) coordinate); or another event such as receiving an e-mail, a phone call, a text message, or any other type of event. In some embodiments, a photograph can be used to document an event or simply to save contextual information in the first track 560. A second event 522 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 562 can include continuously collected cognitive state data such as electrodermal activity data 530. A third track 564 can include facial data. The facial data can be collected intermittently when the individual is looking toward a camera. The facial data 540 can include one or more still photographs, videos, or abstracted facial expressions which can be collected when the user looks in the direction of the camera. A fourth track 566 can include facial data that is collected either intermittently or continuously by a second camera. The facial data 542 can include one or more still photographs, videos, or abstracted facial expressions which can be collected when the user looks in the direction of that camera. A fifth track 568 can include facial data that is collected from a third camera, such as the webcam. In the example shown, the fifth track 568 includes first facial data 544, second facial data 546, and third facial data 548, which can be any type of facial data including data that can be used for determining cognitive state information. Any number of samples of facial data can be collected in any track. The cognitive state data from the various tracks can be collected simultaneously, collected on one track exclusive of other tracks, collected where cognitive state data overlaps between the tracks, and so on. When cognitive state data from multiple tracks overlap, one track's data can take precedence or the data from the multiple tracks can be combined.

Additional tracks, through the $n^{th}$ track 570, of cognitive state data of any type can be collected. The additional tracks 570 can be collected on a continuous or on an intermittent basis. The intermittent basis can be either occasional or periodic. Analysis can further comprise interpolating cognitive state data when the cognitive state data collected is intermittent, and/or imputing additional cognitive state data where the cognitive state data is missing. One or more interpolated tracks 572 can be included and can be associated with cognitive state data that is collected on an intermittent basis, such as the facial data of the fifth track 568. Interpolated data 550 and further interpolated data 552 can contain interpolations of the facial data of the fifth track 568 for the time periods where no facial data was collected in that track. Other embodiments interpolate data for periods where no track includes facial data. In other embodiments, analysis includes interpolating cognitive state analysis when the cognitive state data collected is intermittent.

The cognitive state data, such as the continuous cognitive state data 530 and/or any of the collected facial data 540, 542, 544, 546, and 548, can be tagged. The tags can include metadata related to the cognitive state data, including, but not limited to, the device that collected the cognitive state data; the individual from whom the cognitive state data was collected; the task being performed by the individual; the media being viewed by the individual; and the location, environcognitive conditions, time, date, or any other contextual information. The tags can be used to locate pertinent cognitive state data; for example, the tags can be used to retrieve the cognitive state data from a database. The tags can be included with the cognitive state data that is sent over the internet to cloud or web-based storage and/or services. As such the tags can be used locally on the machine where the cognitive state data was collected and/or remotely on a remote server or a cloud/web service.

Other tags can be related to the cognitive state data. Further embodiments can include tagging the cognitive state data with sensor data. The sensor data can be obtained from the vehicle occupant along with the video data or the audio data, instead of the video data or the audio data, etc. In embodiments, the sensor data can include one or more of vehicle temperature, outside temperature, time of day, level of daylight, weather conditions, headlight activation, windshield wiper activation, entertainment center selection, or entertainment center volume. Other sensor data can include physiological data related to one or more occupants of the vehicle. The physiological data can include heart rate, heart rate variability, electrodermal activity, acceleration, and the like. The tags can also be related to the cognitive state that can be determined by image-based analysis of the video, audio, or physiological data, or other techniques. In embodiments, the tags that can be applied can be based on one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 6:
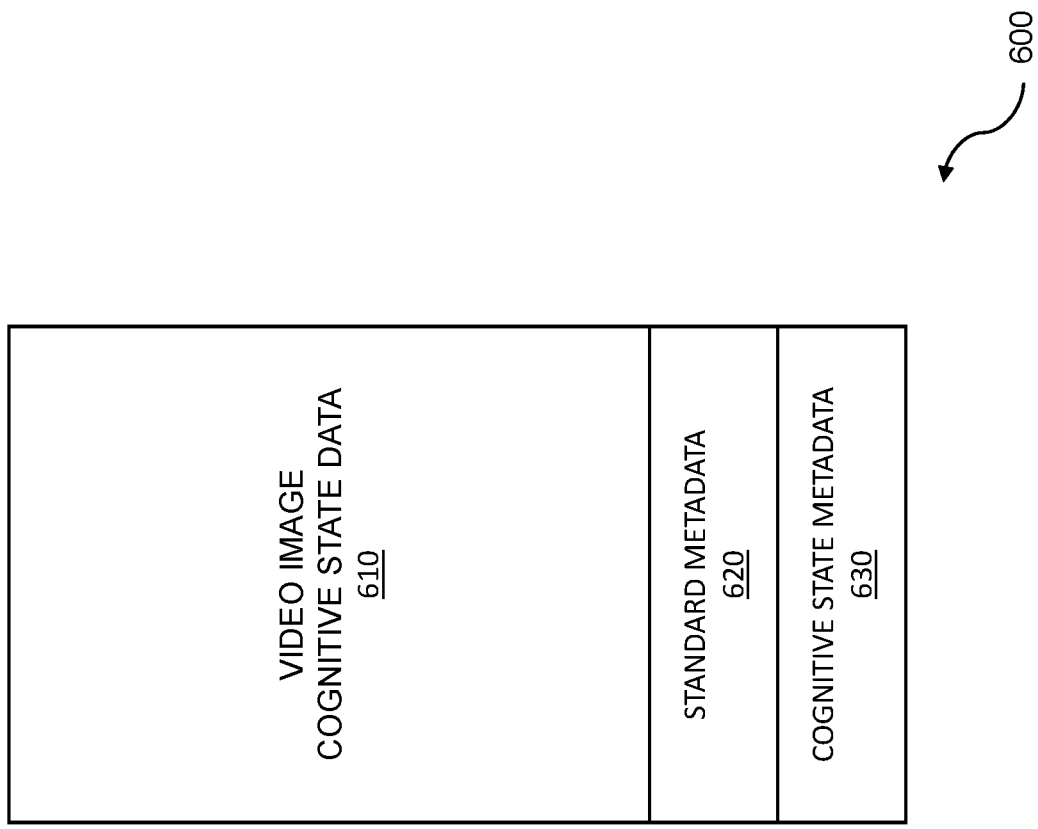
FIG. 6 shows cognitive state data with tags.

FIG. 6 shows cognitive state data with tags. Cognitive state data, including cognitive state data with tags, can be used for vehicle manipulation using near-infrared image processing. Images including facial data of a vehicle occupant are obtained using imaging devices within a vehicle. The images include visible light images and near-infrared images. A classifier is trained using the visible light image content. The classifier can be modified based on the near-infrared content. The classifier is deployed for analysis of additional images. The additional images are analyzed to determine cognitive state, and the vehicle is manipulated based on the cognitive state. The cognitive state data, such as the cognitive state data with tags 600, includes video image cognitive state data 610 captured on an individual from a first source. In some embodiments, the source of the cognitive state data includes certain standard metadata 620 with the cognitive state data 610. For example, a video camera which includes timestamps along with video data demonstrates such metadata inclusion. A still camera which includes EXIF (or Exif) data identifying the camera model, exposure information, and day and date information in the JPEG or other image file format containing the compressed image data shows another instance of metadata inclusion.

In embodiments, additional data which provides information about the cognitive state data 610 is determined. Such additional data can be tagged to the cognitive state data as cognitive state metadata 630. The cognitive state metadata 630 can provide information about the cognitive states useful in the analysis of the cognitive state data 610. In embodiments, the cognitive state can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state metadata 630, or additional data, is data that is not tagged to the cognitive state data by the source of the cognitive state data and not always known to the source of the cognitive state data 610. Thus, the cognitive state metadata 630 is tagged to the cognitive state data 610 by an entity that is not the original source of the cognitive state data.

In one embodiment, a video camera is used to capture the cognitive state data 610. The video camera can include standard metadata 620 such as time and date and model number of the camera, along with the video image, which in this case comprises video image cognitive state data 610, in a MPEG-4 data stream that is sent from the video camera to a cognitive state data collection machine. The standard metadata 620 can be included using standard metadata formats defined by the MPEG-4 specification. The cognitive state data collection machine can determine an identity of the individual being monitored, based on a login ID, and an activity of that individual, such as watching a particular media presentation. The cognitive state data collection machine can then tag the video image with the login ID and the name of the particular media presentation as cognitive state metadata 630. In at least one embodiment, the cognitive state data collection machine formats the cognitive state metadata as XMP metadata and includes it in the MPEG-4 file. Other embodiments determine different additional information to be used as cognitive state metadata 630 and employ different formats to tag the cognitive state data 610 with the cognitive state metadata 630.

Once the data collection machine has captured cognitive state data, at least a portion of the cognitive state data tagged with the additional data is sent to a web service. The portion of the cognitive state data sent to the web service can be based on the additional contextual data collected or can be based on cognitive state metadata 630. At the web service, portions of cognitive state data can be selected for analysis based, at least in part, on tags identifying one or more contexts. In at least one embodiment, the selected portions are based, at least in part, on identifying a particular individual. In some embodiments, the selected portions include tags identifying at least two different timestamps so that samples can be distributed over a period of time. In some embodiments, the selected portions are based, at least in part, on tags identifying a particular context. Once the portions are selected, they can be analyzed by the web service and can be used to create cognitive state information.

Figure 7:
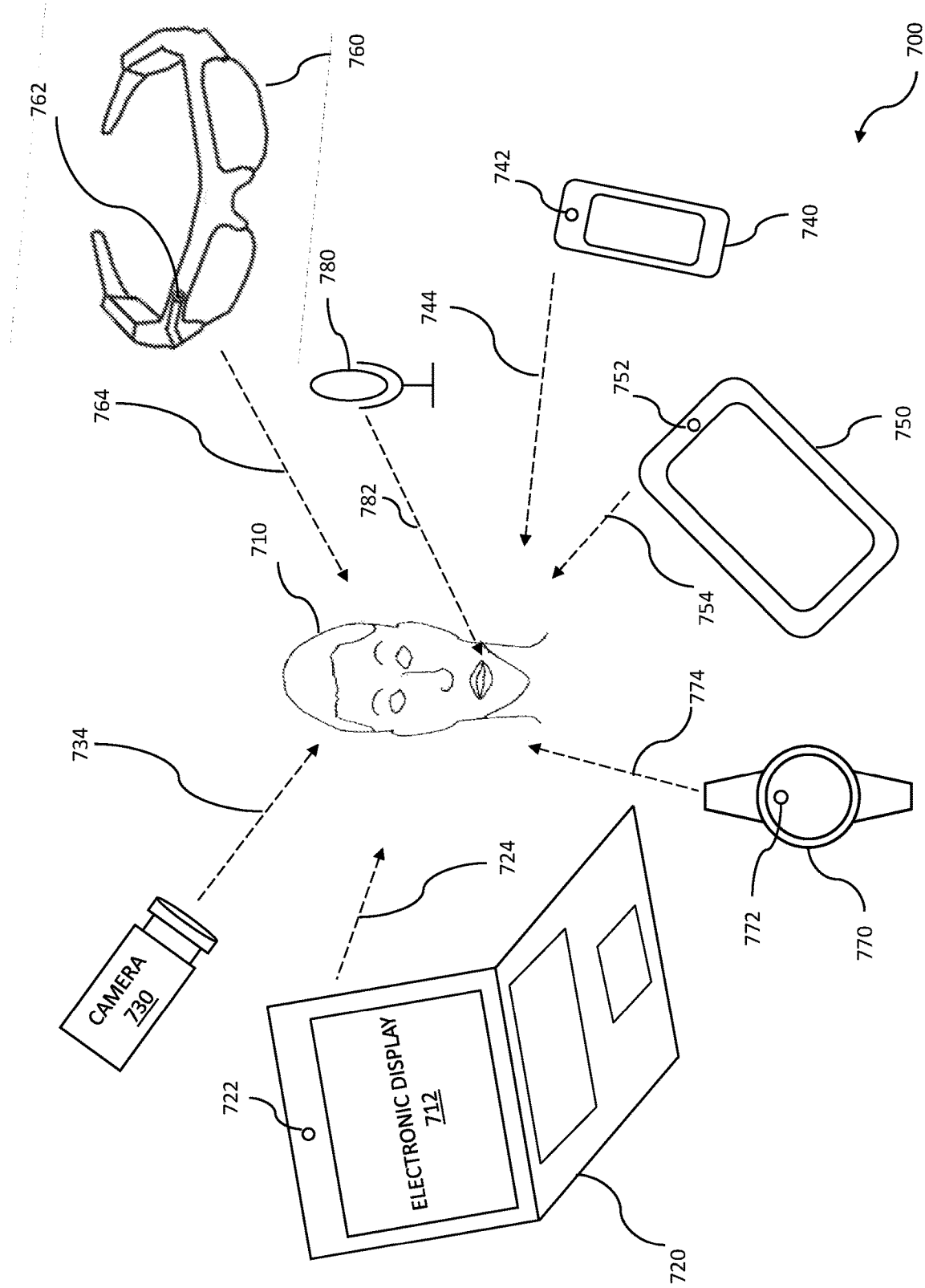
FIG. 7 shows example image and audio collection including multiple mobile devices.

FIG. 7 is a diagram showing image collection including multiple mobile devices. Cognitive state data including image data and audio data can be collected using multiple mobile devices. The collected cognitive state data can be used for cognitive state vehicle manipulation using near-infrared image processing. Visible light images and near-infrared images, which include facial data, are obtained from a vehicle occupant. A classifier is trained or modified based on visible light content of the images or near-infrared content of the images. The classifier is deployed and used to analyze additional images that include near-infrared images. The analysis is used to determine a cognitive state. The vehicle is manipulated based on the cognitive state. While one person is shown, in practice the video data or audio data on any number of people can be collected. In the diagram 700, the multiple mobile devices can be used separately or in combination to collect video data, audio data, or both video data and audio data on a user 710. While one person is shown, the video data and audio data can be collected on multiple people. A user 710 can be observed as she or he is performing a task, experiencing an event, viewing a media presentation, and so on. The user 710 can be shown one or more media presentations, political presentations, social media, or another form of displayed media. The one or more media presentations can be shown to a plurality of people. The media presentations can be displayed on an electronic display 712 or another display. The data collected on the user 710 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 710 can be analyzed and viewed for a variety of purposes including expression analysis, cognitive state analysis, mental state analysis, emotional state analysis, and so on. The electronic display 712 can be on a laptop computer 720 as shown, a tablet computer 750, a cell phone 740, a television, a mobile monitor, or any other type of electronic device. In one embodiment, video data including expression data is collected on a mobile device such as a cell phone 740, a tablet computer 750, a laptop computer 720, or a watch 770. Similarly, the audio data including speech data and non-speech vocalizations can be collected on one or more of the mobile devices. Thus, the multiple sources can include at least one mobile device, such as a phone 740 or a tablet 750, or a wearable device such as a watch 770 or glasses 760. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 722, a phone camera 742, a tablet camera 752, a wearable camera 762, and a mobile camera 730. A wearable camera can comprise various camera devices, such as a watch camera 772. Sources of audio data 782 can include a microphone 780.

As the user 710 is monitored, the user might move due to the nature of the task, boredom, discomfort, distractions, or for another reason. As the user moves, the camera with a view of the user's face can be changed. Thus, as an example, if the user is looking in a first direction, the line of sight 724 from the webcam 722 is able to observe the user's face, but if the user is looking in a second direction, the line of sight 734 from the mobile camera 730 is able to observe the user's face. Furthermore, in other embodiments, if the user is looking in a third direction, the line of sight 744 from the phone camera 742 is able to observe the user's face, and if the user is looking in a fourth direction, the line of sight 754 from the tablet camera 752 is able to observe the user's face. If the user is looking in a fifth direction, the line of sight 764 from the wearable camera 762, which can be a device such as the glasses 760 shown and can be worn by another user or an observer, is able to observe the user's face. If the user is looking in a sixth direction, the line of sight 774 from the wearable watch-type device 770, with a camera 772 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 710 can also use a wearable device including a camera for gathering contextual information and/or collecting expression data on other users. Because the user 710 can move her or his head, the facial data can be collected intermittently when she or he is looking in a direction of a camera. In some cases, multiple people can be included in the view from one or more cameras, and some embodiments include filtering out faces of one or more other people to determine whether the user 710 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device.

The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 8:
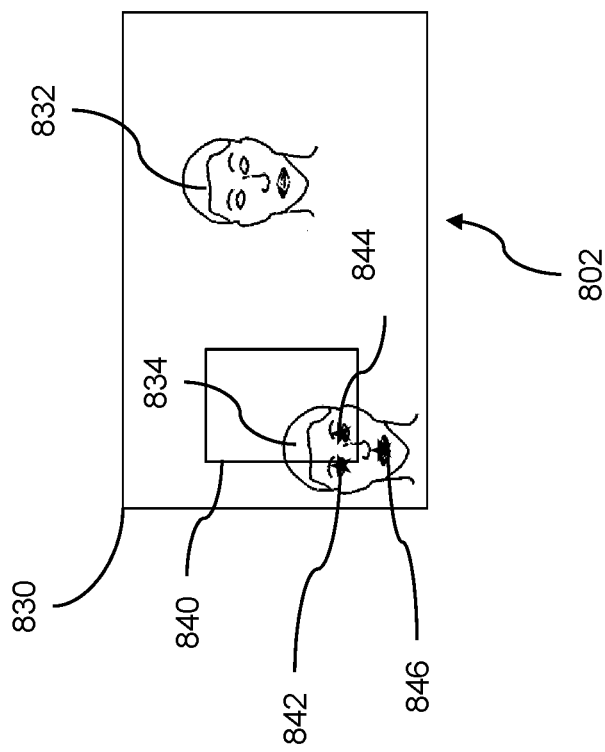
FIG. 8 illustrates feature extraction for multiple faces.
Figure 8:
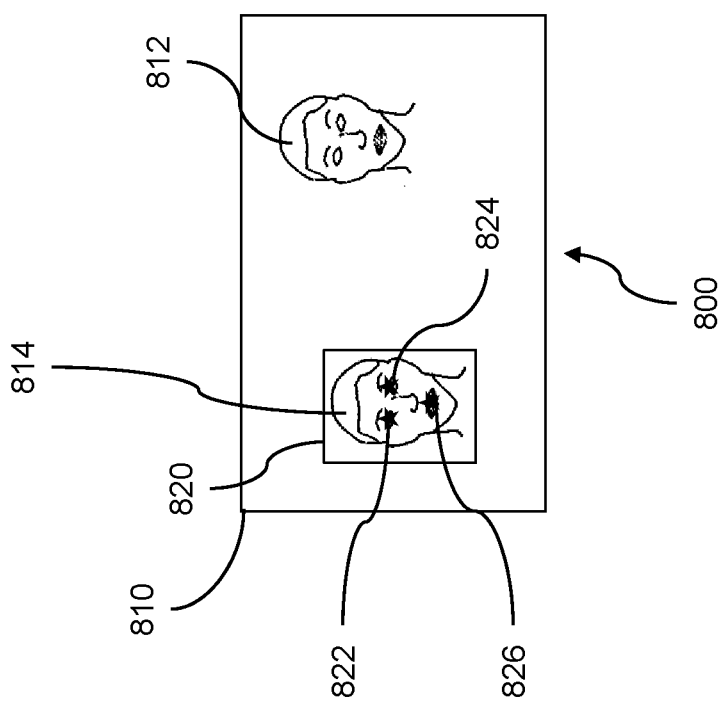

FIG. 8 illustrates feature extraction for multiple faces. Image analysis, including facial analysis, can be based on feature extraction from multiple faces. Feature extraction for one or more faces can be applied to cognitive state vehicle manipulation. Images such as visible light images and near-infrared images can include facial data of a vehicle occupant. The images can be obtained using imaging devices within the vehicle. A classifier is trained or modified based on the visible light image content or the near-infrared image content. The classifier is deployed for analysis of additional images such as near-infrared images. The analysis is used to determine a cognitive state. The vehicle is manipulated based on the cognitive state.

The feature extraction for multiple faces can be performed for faces that can be detected in multiple images. In embodiments, the features of multiple faces are extracted for evaluating cognitive states. Features of a face or a plurality of faces can be extracted from collected video data. The feature extraction can be performed by analysis, by using one or more processors, by using one or more video collection devices, and by using a server. The analysis device can be used to perform face detection for a second face, as well as to perform facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or existing observation, sample, datum, etc. should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When a new observation is received, then the classifier can be used to categorize the new observation. Classifiers can be used for many analysis applications, including analysis of one or more faces. The use of classifiers can be the basis of analyzing the one or more faces for gender, ethnicity, and age; of detecting the one or more faces in one or more videos; of detecting facial features and landmarks; and so on. The observations can be analyzed based on one or more of a set of quantifiable properties. The properties can be described as features and explanatory variables involving various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, etc. Algorithms for classification can be implemented using a variety of techniques, including neural networks, kernel estimation, support vector machines, use of quadratic surfaces, and so on. Classification can be used in many application areas such as computer vision, and speech and handwriting recognition. Classification can be used for biometric identification of one or more people in a single frame or in multiple frames of one or more videos.

Returning to FIG. 8, the detection of the first face, the second face, and multiple faces can include identifying facial landmarks, generating a bounding box, and predicting a bounding box and landmarks for a next frame, where the next frame can be one of a plurality of frames of a video containing faces. A first video frame 800 includes a frame boundary 810, a first face 812, and a second face 814. The video frame 800 also includes a bounding box 820. Facial landmarks can be generated for the first face 812. Face detection can be performed to initialize a second set of locations for a second set of facial landmarks for a second face within the video. Facial landmarks in the video frame 800 can include the facial landmarks 822, 824, and 826. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face and can include estimating a second rough bounding box for the second face based on the facial landmark detection. The estimating of a second rough bounding box can include the bounding box 820. Bounding boxes can also be estimated for one or more other faces within the boundary 810. The bounding box can be refined, as can the one or more facial landmarks. The refining of the second set of locations for the second set of facial landmarks can be based on localized information around the second set of facial landmarks. The bounding box 820 and the facial landmarks 822, 824, and 826 can be used to estimate future locations for the second set of locations for the second set of facial landmarks in a future video frame from the first video frame.

A second video frame 802 is also shown. The second video frame 802 includes a frame boundary 830, a first face 832, and a second face 834. The second video frame 802 also includes a bounding box 840 and the facial landmarks, or points, 842, 844, and 846. In other embodiments, multiple facial landmarks are generated and used for facial tracking of the two or more faces of a video frame, such as the shown second video frame 802. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either the first face, the second face, or both faces, and so on. Other facial points can correspond to the second face. As mentioned above, multiple facial points can be determined within a frame. One or more of the other facial points that are determined can correspond to a third face. The location of the bounding box 840 can be estimated, where the estimating can be based on the location of the generated bounding box 820 shown in the first video frame 800. The three facial points shown, facial points, or landmarks, 842, 844, and 846, might lie within the bounding box 840 or might not lie partially or completely within the bounding box 840. For instance, the second face 834 might have moved between the first video frame 800 and the second video frame 802. Based on the accuracy of the estimating of the bounding box 840, a new estimation can be determined for a third, future frame from the video, and so on. The evaluation can be performed, all or in part, using semiconductor-based logic.

Figure 9:
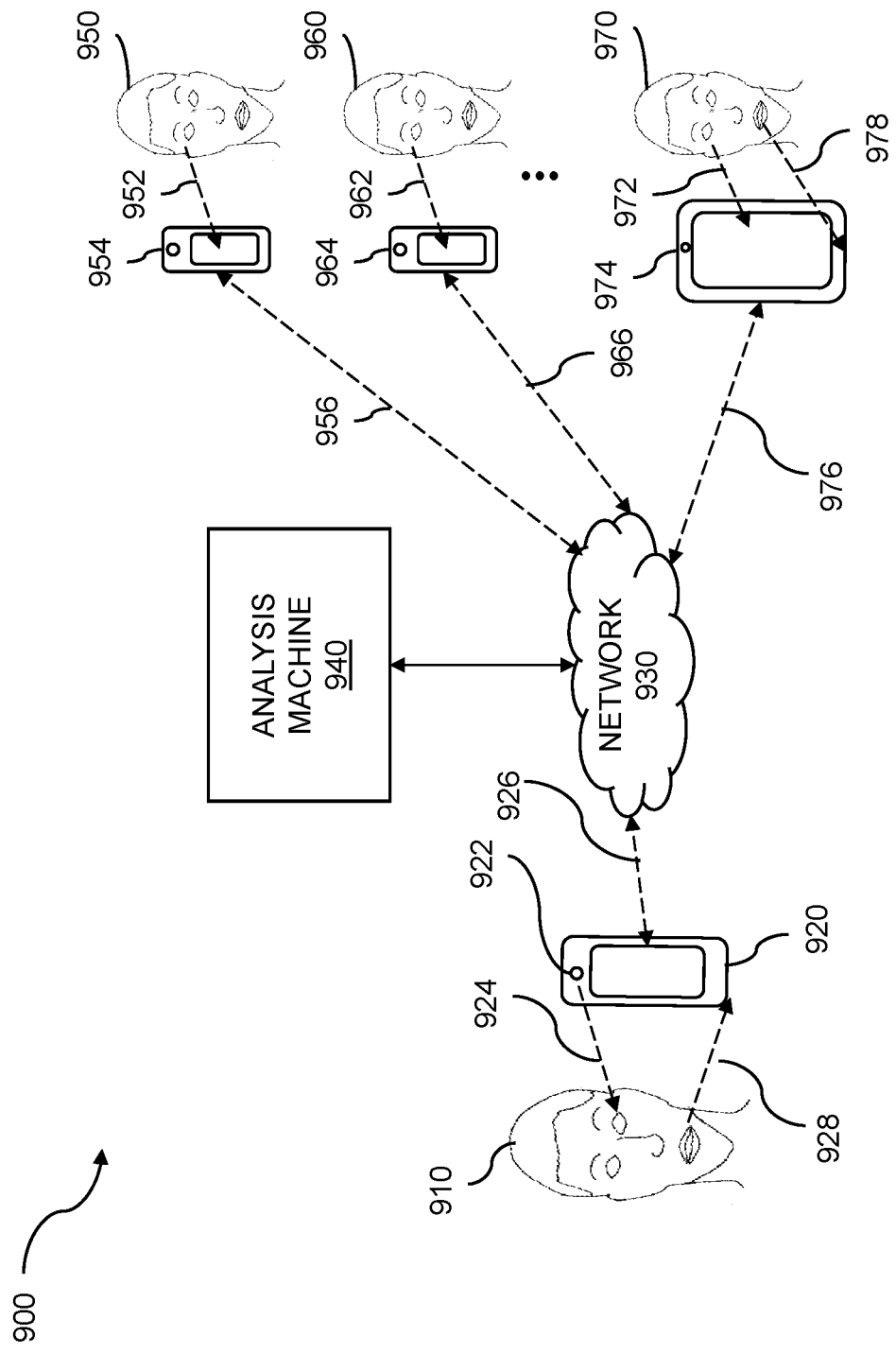
FIG. 9 shows an example of live streaming of social video and audio.

FIG. 9 shows an example of live streaming of social video and audio. The streaming of social video and social audio can be applied to cognitive state vehicle manipulation using near-infrared image processing. The live streaming can include cognitive state data, image data, facial data, speech data, audio data, etc. The cognitive state data can be determined by obtaining and analyzing images including facial data from a vehicle occupant. A classifier is trained or modified and deployed for analysis of additional images including near-infrared images. The additional images are analyzed to determine a cognitive state, and the vehicle is manipulated based on the cognitive state. The live streaming and image analysis can be facilitated by a video capture device, a local server, a remote server, a semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams, such as webcasts, online classes, sporting events, news, computer gaming, or video conferences can be scheduled, while others can be impromptu streams that are broadcast as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 900 shows a user 910 broadcasting a video live stream and an audio live stream to one or more people as shown by a first person 950, a second person 960, and a third person 970. A portable, network-enabled, electronic device 920 can be coupled to a front-facing camera 922. The portable electronic device 920 can be a smartphone, a PDA, a tablet, a laptop computer, and so on. The camera 922 coupled to the device 920 can have a line-of-sight view 924 to the user 910 and can capture video of the user 910. The portable electronic device 920 can be coupled to a microphone (not shown). The microphone can capture voice data 928 such as speech and non-speech vocalizations. In embodiments, non-speech vocalizations can include grunts, yelps, squeals, snores, sighs, laughter, filled pauses, unfilled pauses, yawns, or the like. The captured video and audio can be sent to an analysis or recommendation engine 940 using a network link 926 to the Internet 930. The network link can be a wireless link, a wired link, and so on. The recommendation engine 940 can recommend to the user 910 an app and/or platform that can be supported by the server and can be used to provide a video live stream, an audio live stream, or both a video live stream and an audio live stream to one or more followers of the user 910.

In the example 900, the user 910 has three followers: a first person 950, a second person 960, and a third person 970. Each follower has a line-of-sight view to a video screen on a portable, networked electronic device. In other embodiments, one or more followers follow the user 910 using any other networked electronic device, including a computer. In the example 900, a first person 950 has a line-of-sight view 952 to the video screen of a device 954; a second person 960 has a line-of-sight view 962 to the video screen of a device 964, and a third person 970 has a line-of-sight view 972 to the video screen of a device 974. The device 974 can also capture audio data 978 from the third person 970. The portable electronic devices 954, 964, and 974 can each be a smartphone, a PDA, a tablet, and so on. Each portable device can receive the video stream and the audio stream being broadcast by the user 910 through the Internet 930 using the app and/or platform that can be recommended by the recommendation engine 940. The device 954 can receive a video stream and the audio stream using the network link 956, the device 964 can receive a video stream and the audio stream using the network link 966, the device 974 can receive a video stream and the audio stream using the network link 976, and so on. The network link can be a wireless link, a wired link, a hybrid link, and so on. Depending on the app and/or platform that can be recommended by the recommendation engine 940, one or more followers, such as the followers shown 950, 960, and 970, can reply to, comment on, or otherwise provide feedback to the user 910 using their respective devices 954, 964, and 974.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 10:
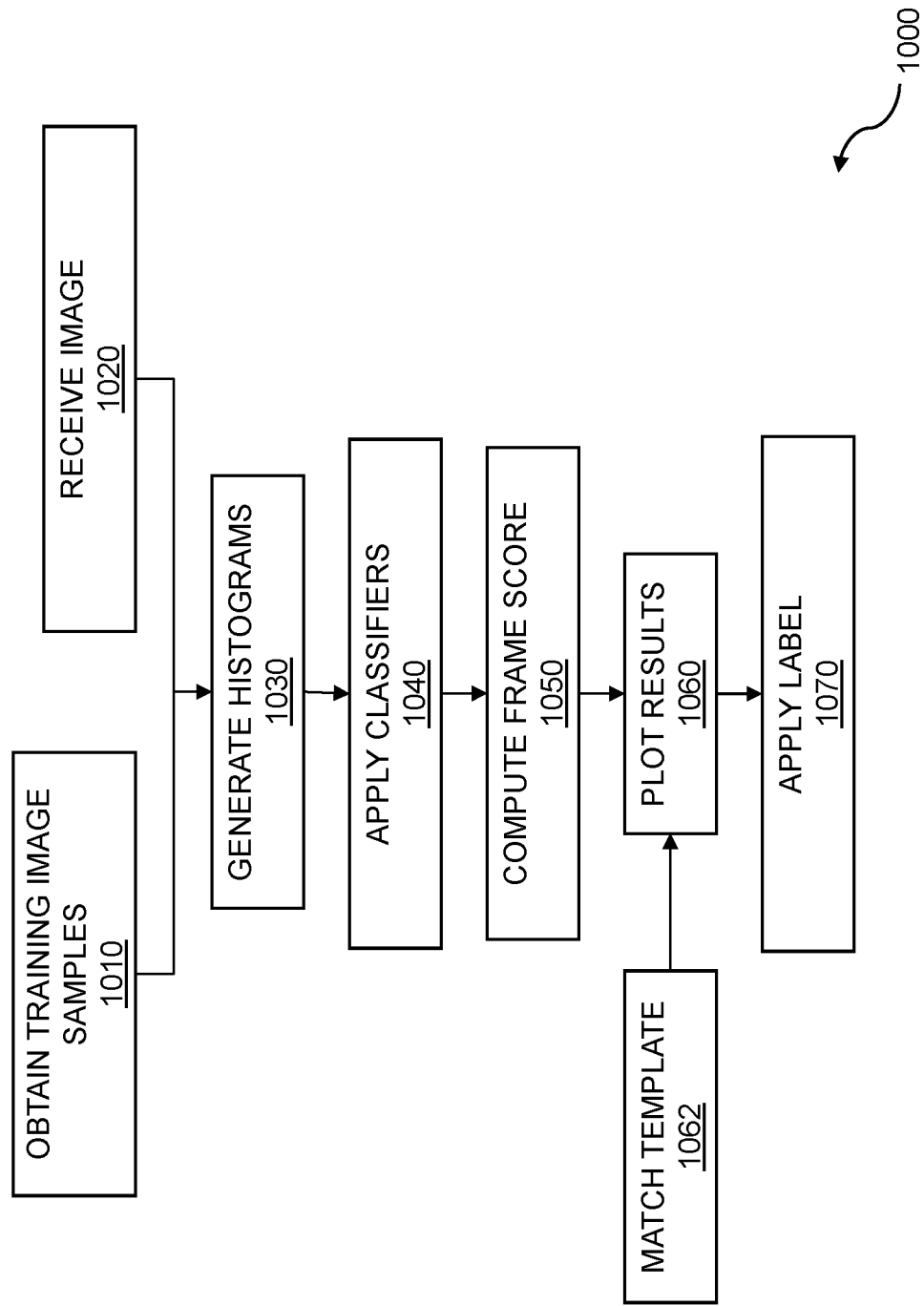
FIG. 10 is a flow diagram for detecting facial expressions.

FIG. 10 is a flow diagram for detecting facial expressions. Cognitive states can be determined by detecting and analyzing facial expressions in images. The cognitive states can be used for vehicle manipulation, where the vehicle manipulation can use near-infrared image processing. One or more images including facial data are obtained from a vehicle occupant by using in-vehicle imaging devices. The images include visible light images and near-infrared images. A classifier is trained or modified based on the visible light content of the images or the near-infrared content of the images. The classifier is deployed for analysis of additional images which can include near-infrared images. The additional images are analyzed to determine a cognitive state, and the vehicle is manipulated based on the cognitive state. The flow 1000, or portions thereof, can be implemented in semiconductor logic, can be accomplished using a mobile device, can be accomplished using a server device, and so on. The flow 1000 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on the determination of action units (AU), where the action units are determined using FACS coding. The AUs can be used separately or in combination to identify facial expressions. Based on the facial landmarks, one or more AUs can be identified by number and intensity. For example, AU12 can be used to code a lip corner puller and can be used to infer a smirk.

The flow 1000 begins by obtaining training image samples 1010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, a sensor, and so on. The flow 1000 continues with receiving an image 1020. The image 1020 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1000 continues with generating histograms 1030 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1000 continues with applying classifiers 1040 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1000 continues with computing a frame score 1050. The score computed for an image, where the image can be a frame from a video, can be used to determine the presence of a facial expression in the image or video frame. The score can be based on one or more versions of the image 1020 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1000 continues with plotting results 1060. The results that are plotted can include one or more scores for one or more frames computed over a given time t. For example, the plotted results can include classifier probability results from analysis of HoGs for a sequence of images and video frames. The plotted results can be matched with a template 1062. The template can be temporal and can be represented by a centered box function or another function. A best fit with one or more templates can be found by computing a minimum error. Other best-fit techniques can include polynomial curve fitting, geometric curve fitting, and so on. The flow 1000 continues with applying a label 1070. The label can be used to indicate that a particular facial expression has been detected in the one or more images or video frames which constitute the image 1020 that was received. The label can be used to indicate that any of a range of facial expressions has been detected, including a smile, an asymmetric smile, a frown, and so on. Various steps in the flow 1000 may be changed in order, repeated, omitted, or the like without departing from the disclosed concepts. Various embodiments of the flow 1000 can be included in a computer program product embodied in a non-transitory computer readable medium that includes code executable by one or more processors. Various embodiments of the flow 1000, or portions thereof, can be included on a semiconductor chip and implemented in special purpose logic, programmable logic, and so on.

Figure 11:
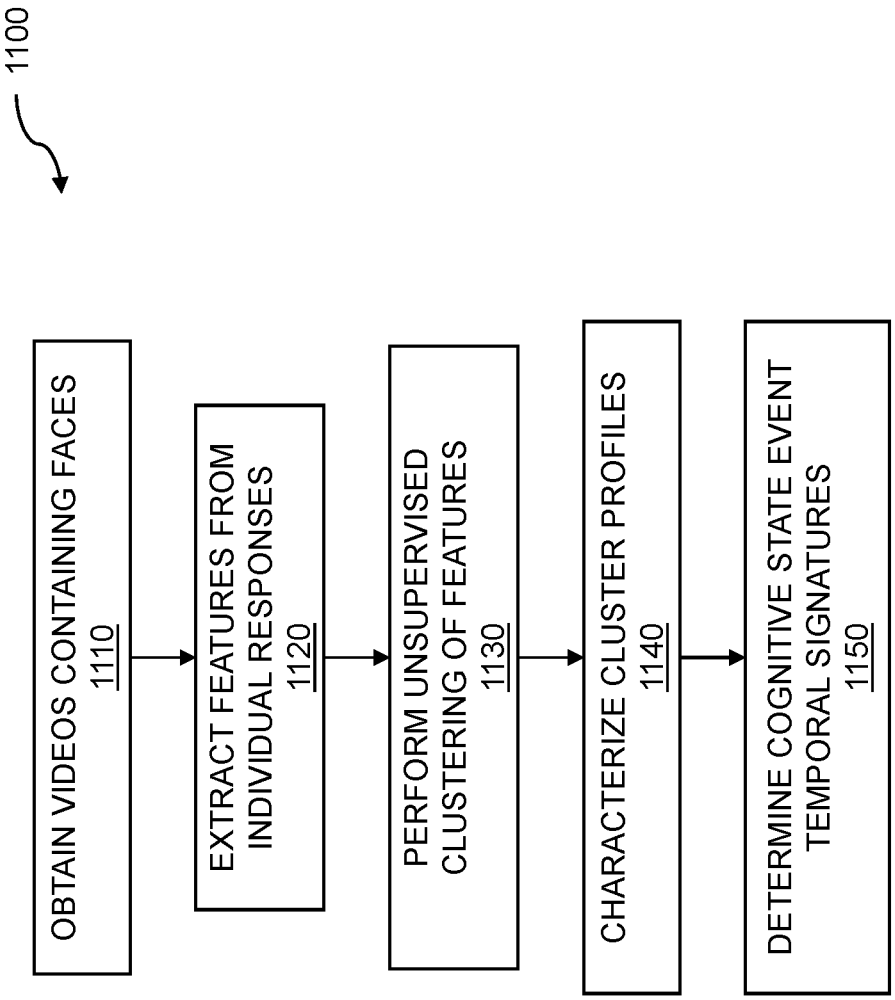
FIG. 11 is a flow diagram for the large-scale clustering of facial events.

FIG. 11 is a flow diagram for the large-scale clustering of facial events. Cognitive state vehicle manipulation can be based on image-based analysis, where the analysis can use results from large-scale clustering. Images including facial data are obtained from a vehicle occupant. The images can include visible light based images and near-infrared based images. A classifier is trained based the visible light image content or the near-infrared image content. The classifier is deployed for analysis of additional images. The additional images are analyzed to determine a cognitive state, and the vehicle is manipulated based on the cognitive state. Cognitive state events can include facial events, speech events, etc. The large-scale clustering of facial events can be performed for data collected from a remote computing device. The facial events can be collected from people as they interact with a vehicle. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1100 includes obtaining videos containing faces 1110. The videos can be obtained using one or more cameras, where the cameras can include a webcam coupled to one or more devices employed by the one or more people using the web-based framework. The flow 1100 continues with extracting features from the individual responses 1120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1100 continues with performing unsupervised clustering of features 1130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1100 includes characterizing cluster profiles 1140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared across various demographic groups, where the groups can be formed based on geographic location, age, ethnicity, gender, and so on.

The flow 1100 can include determining cognitive state event temporal signatures 1150. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1100 may be changed in order, repeated, omitted, or the like without departing from the disclosed concepts. Various embodiments of the flow 1100 can be included in a computer program product embodied in a non-transitory computer readable medium that includes code executable by one or more processors. Various embodiments of the flow 1100, or portions thereof, can be included on a semiconductor chip and implemented in special purpose logic, programmable logic, and so on.

Figure 12:
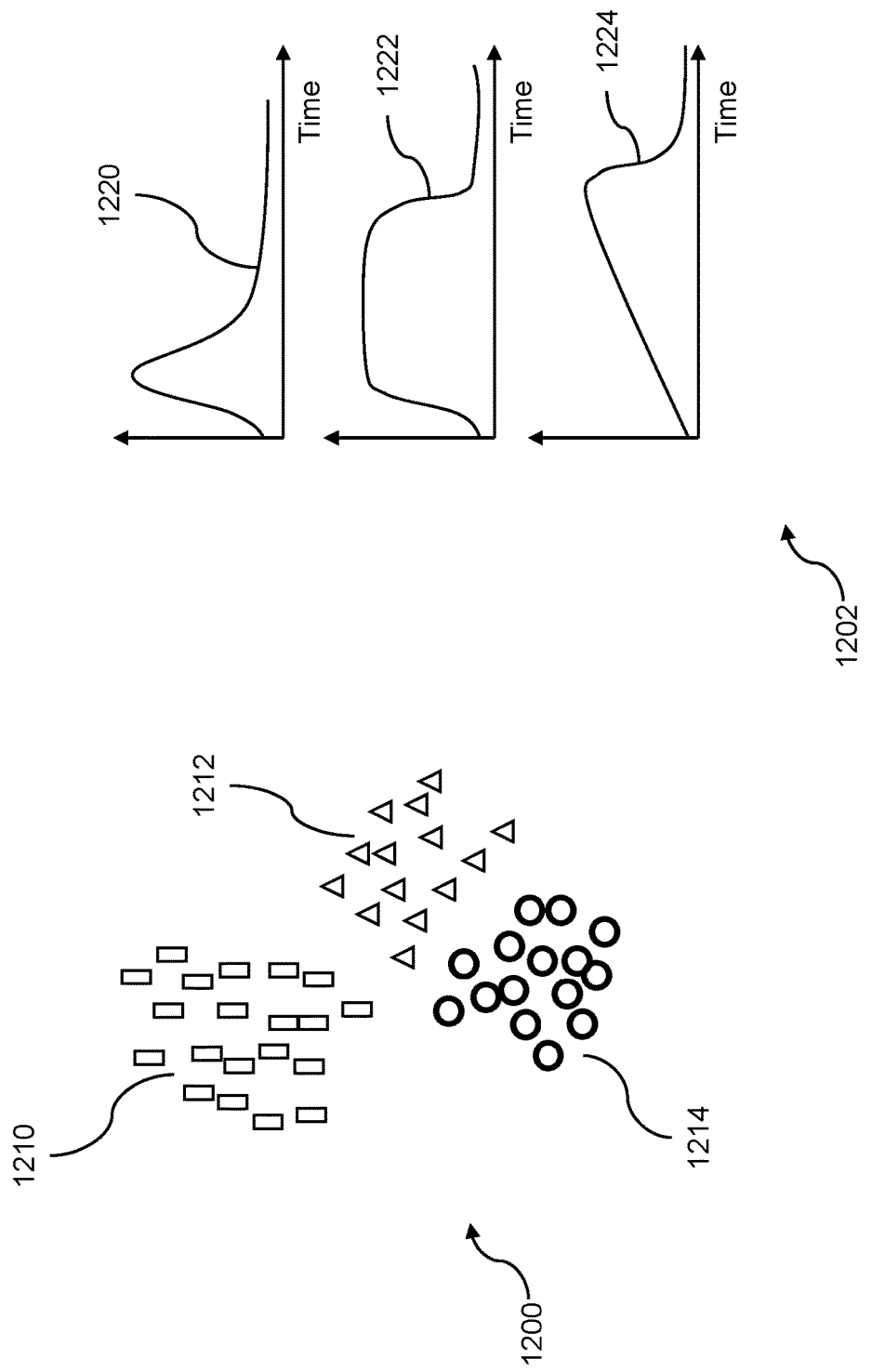
FIG. 12 shows unsupervised clustering of features and characterizations of cluster profiles.

FIG. 12 shows unsupervised clustering of features and characterizations of cluster profiles. Features and characterizations can be applied to cognitive state based vehicle manipulation, where the vehicle manipulation uses near-infrared image processing. Vehicle occupant images are obtained, where the images include facial data. The images include visible-light based images and near-infrared based images. A classifier is trained and can be modified based on the image contents. The classifier is deployed and used for analyzing additional images to determine a cognitive state. The vehicle is manipulated based on the cognitive state. The clustering of features and characterizations of cluster profiles can be performed for data collected from a remote computing device. The clustering of features and characterizations of cluster profiles can be performed for people as they interact with a vehicle. The subsectional components can be used with performing the evaluation of content of the face. The subsectional components can be used to provide a context. Features including samples of facial data can be clustered using unsupervised clustering. Various clusters can be formed which include similar groupings of facial data observations. The example 1200 shows three clusters, clusters 1210, 1212, and 1214. The clusters can be based on video collected from people who have opted-in to video collection. When the data collected is captured using a web-based framework, the data collection can be performed on a grand scale, including hundreds, thousands, or even more participants who can be situated locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1202 can be generated based on the clusters that can be formed from unsupervised clustering, with time shown on the x-axis and intensity or frequency shown on the y-axis. The cluster profiles can be based on captured facial data, including facial expressions. The cluster profile 1220 can be based on the cluster 1210, the cluster profile 1222 can be based on the cluster 1212, and the cluster profile 1224 can be based on the cluster 1214. The cluster profiles 1220, 1222, and 1224 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 13A:
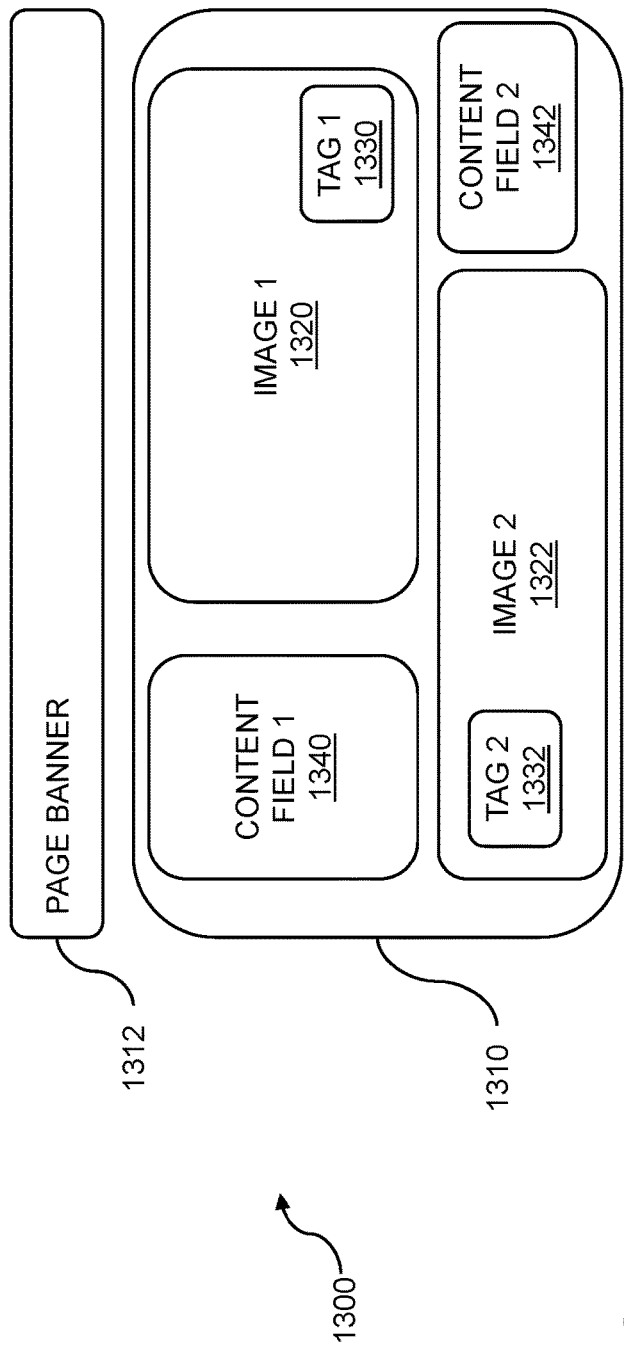
FIG. 13A shows example tags embedded in a webpage.

FIG. 13A shows example tags embedded in a webpage. Cognitive state based vehicle manipulation uses near-infrared image processing. In some embodiments, screens within a vehicle can use embedded tags. Images of a vehicle occupant are obtained using imaging devices within a vehicle. The images include facial data of the vehicle occupant. The images include visible light-based images and near-infrared based images. A classifier is trained using the visible light content of images and can be modified using the near-infrared content from the images. In embodiments, the classifier is trained using the visible light content and the near-infrared content. The classifier is deployed for analysis of additional images, such as near-infrared based images, of the vehicle occupant. The additional images are analyzed to determine a cognitive state, and the vehicle is manipulated based on the cognitive state.

The tags embedded in the webpage can be used for image analysis for data collected from a remote computing device. The tags embedded in the webpage can be used by people as they interact with a vehicle. Once a tag is detected, a mobile device, a server, semiconductor-based logic, etc. can be used to evaluate associated facial expressions. A webpage 1300 can include a page body 1310, a page banner 1312, and so on. The page body can include one or more objects, where the objects can include text, images, videos, audio, and so on. The example page body 1310 shown includes a first image, image 1 1320; a second image, image 2 1322; a first content field, content field 1 1340; and a second content field, content field 2 1342. In practice, the page body 1310 can contain multiple images and content fields and can include one or more videos, one or more audio presentations, and so on. The page body can include embedded tags, such as tag 1 1330 and tag 2 1332. In the example shown, tag 1 1330 is embedded in image 1 1320, and tag 2 1332 is embedded in image 2 1322. In embodiments, multiple tags are embedded. Tags can also be embedded in content fields, in videos, in audio presentations, etc. When a user mouses over a tag or clicks on an object associated with a tag, the tag can be invoked. For example, when the user mouses over tag 1 1330, tag 1 1330 can then be invoked. Invoking tag 1 1330 can include enabling a camera coupled to a user's device and capturing one or more images of the user as the user views a media presentation (or digital experience). In a similar manner, when the user mouses over tag 2 1332, tag 2 1332 can be invoked. Invoking tag 2 1332 can also include enabling the camera and capturing images of the user. In other embodiments, other actions are taken based on invocation of the one or more tags. Invoking an embedded tag can initiate an analysis technique, post to social media, award the user a coupon or another prize, initiate cognitive state analysis, perform emotion analysis, and so on.

Figure 13B:
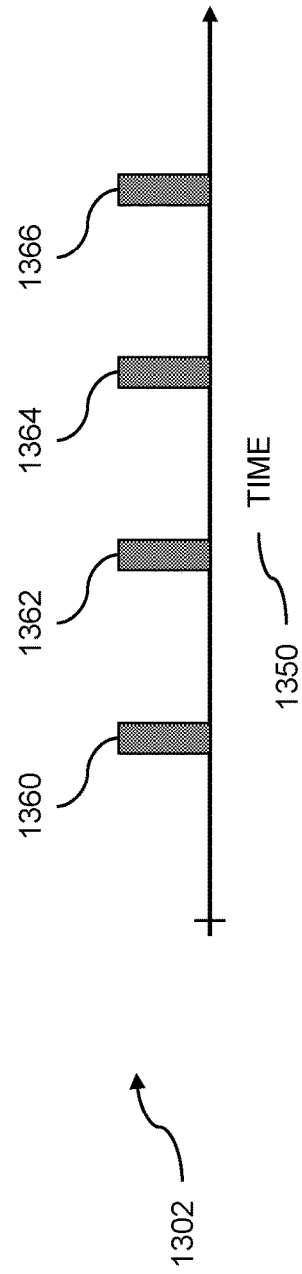
FIG. 13B shows invoking tags to collect images.

FIG. 13B shows invoking tags to collect images. Cognitive state based vehicle manipulation can use near-infrared image processing. The image processing is based on obtaining images including facial data from a vehicle occupant. A classifier is trained based on visible light image content and can be modified based on near-infrared image content. The classifier is deployed, and additional images are analyzed to determine a cognitive state. The vehicle is manipulated based on the cognitive state.

The invoking tags to collect images can be used for image analysis for data collected from a remote computing device. The invoking tags to collect images can be used for people as they interact with a vehicle. As previously stated, a media presentation can be a video, a webpage, and so on. A video 1302 can include one or more embedded tags, such as a tag 1360, a second tag 1362, a third tag 1364, a fourth tag 1366, and so on. In practice, multiple tags can be included in the media presentation. The one or more tags can be invoked during the media presentation. The collection of the invoked tags can occur over time, as represented by a timeline 1350. When a tag is encountered in the media presentation, the tag can be invoked. When the tag 1360 is encountered, invoking the tag can enable a camera coupled to a user device and can capture one or more images of the user viewing the media presentation. Invoking a tag can depend on an opt-in by the user. For example, if a user has agreed to participate in a study by indicating an opt-in, then the camera coupled to the user's device can be enabled and one or more images of the user can be captured. If the user has not agreed to participate in the study and has indicated an opt-out, then invoking the tag 1360 neither enables the camera nor captures images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages, advertising messages, social media sharing, etc. and that enable the camera and image capture when invoked would be embedded in the media presentation, social media sharing, and so on. However, tags embedded in the media presentation that are related to advertisements would not enable the camera when invoked. Various other situations of tag invocation are also possible.

Figure 14:
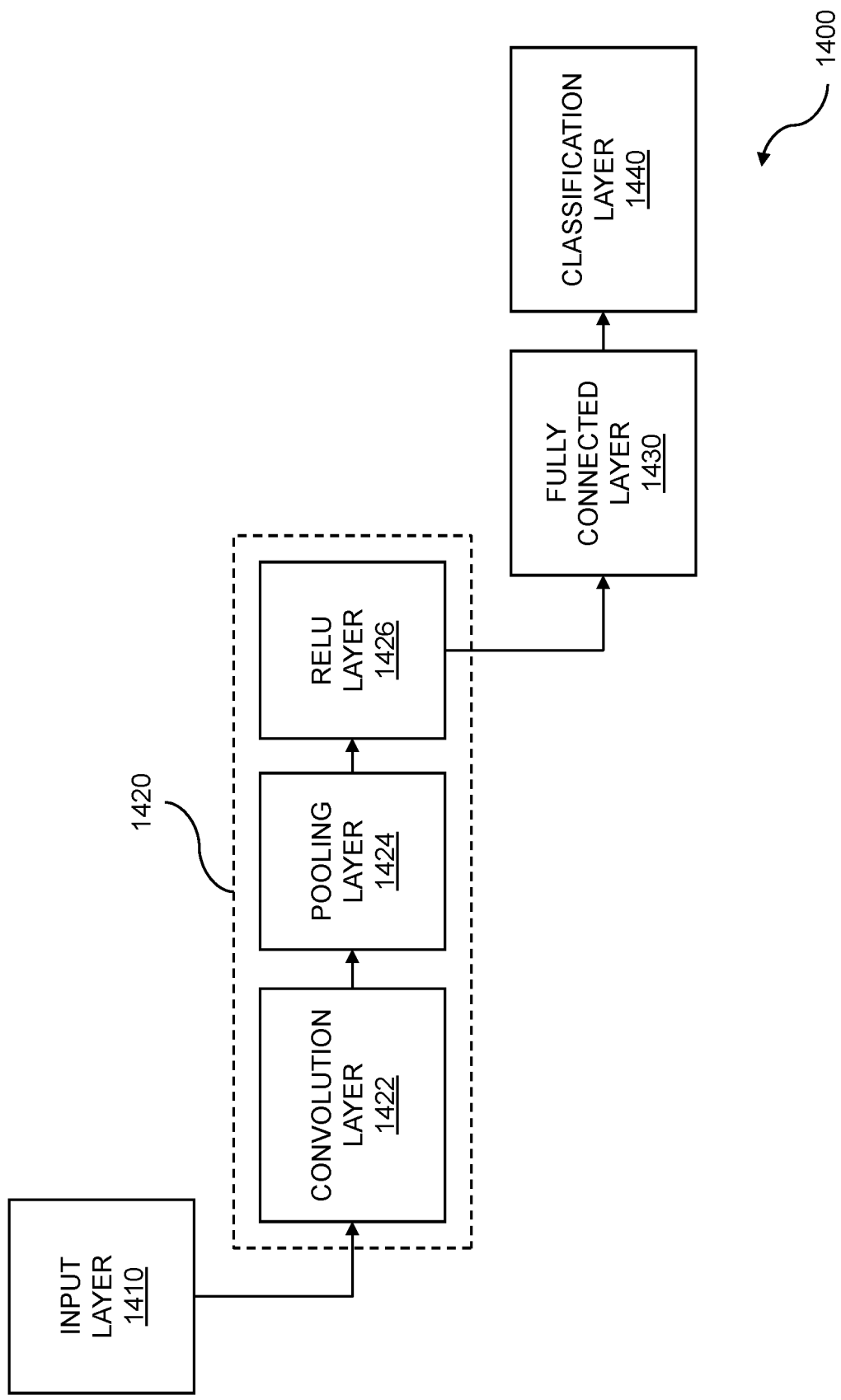
FIG. 14 is an example showing a convolutional neural network (CNN).

FIG. 14 is an example showing a convolutional neural network (CNN). A convolutional neural network such as 1400 can be used for deep learning, where the deep learning can be applied to cognitive state based vehicle manipulation using near-infrared image processing. Images which include facial data are obtained from a vehicle occupant. The images include visible light based images and near-infrared based images. A classifier is trained based on the visible light content of the images. The classifier can be modified based on the near-infrared content. In embodiments, the classifier is trained using the visible light content and the near-infrared content. The classifier is deployed for analyzing additional images which can include near-infrared based images. The additional images are analyzed to determine a cognitive state, and the vehicle is manipulated based on the cognitive state. The convolutional neural network can be applied to tasks such as cognitive state analysis, mental state analysis, mood analysis, emotional state analysis, and so on. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 14 is an example showing a convolutional neural network 1400. The convolutional neural network can be used for deep learning, where the deep learning can be applied to cognitive state based vehicle manipulation using near-infrared image processing. The deep learning system can be accomplished using a convolution neural network or other techniques. The deep learning can accomplish facial recognition and analysis tasks. The network includes an input layer 1410. The input layer 1410 receives image data. The image data can be input in a variety of formats, such as JPEG, TIFF, BMP, and GIF. Compressed image formats can be decompressed into arrays of pixels, wherein each pixel can include an RGB tuple. The input layer 1410 can then perform processing such as identifying boundaries of the face, identifying landmarks of the face, extracting features of the face, and/or rotating a face within the plurality of images.

The network includes a collection of intermediate layers 1420. The multilayered analysis engine can include a convolutional neural network. Thus, the intermediate layers can include a convolution layer 1422. The convolution layer 1422 can include multiple sublayers, including hidden layers within it. The output of the convolution layer 1422 feeds into a pooling layer 1424. The pooling layer 1424 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 1424. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1426. The output of the pooling layer 1424 can be input to the RELU layer 1426. In embodiments, the RELU layer implements an activation function such as $f(x)-\max(0, x)$, thus providing an activation with a threshold at zero. In some embodiments, the RELU layer 1426 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1422 and one or more hidden layers, and wherein the multilayered analysis engine can be used for emotional analysis.

The example 1400 includes a fully connected layer 1430. The fully connected layer 1430 processes each pixel/data point from the output of the collection of intermediate layers 1420. The fully connected layer 1430 takes all neurons in the previous layer and connects them to every single neuron it has. The output of the fully connected layer 1430 provides input to a classification layer 1440. The output of the classification layer 1440 provides a facial expression and/or cognitive state as its output. Thus, a multilayered analysis engine such as the one depicted in FIG. 14 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adaptively learn, as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include the person being more engaged, where engagement is based on affect, the person spending more time playing an online game or navigating a webpage, the person converting by buying a product or service, and so on. The reinforced learning can be based on exploring a solution space and adapting the model, algorithm, etc., which stem from outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 15:
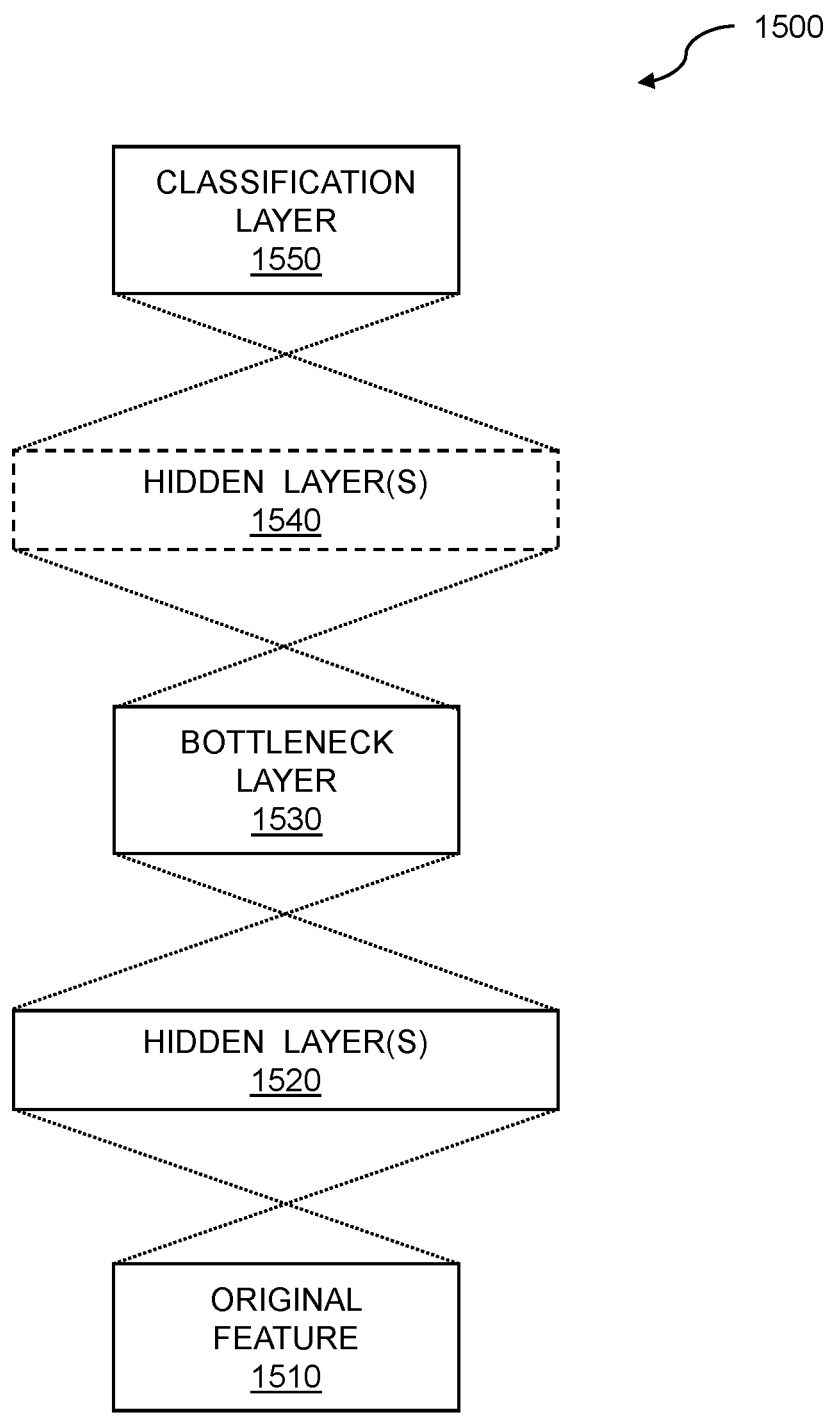
FIG. 15 illustrates a bottleneck layer within a deep learning environment.

FIG. 15 illustrates a bottleneck layer within a deep learning environment. A plurality of layers in a deep neural network (DNN) can include a bottleneck layer. The bottleneck layer can be used for cognitive state vehicle manipulation using near-infrared image processing. A deep neural network can apply classifiers such as image classifiers, facial classifiers, audio classifiers, speech classifiers, and so on. The classifiers can be learned by analyzing cognitive state data. Images of a vehicle occupant are obtained, where the images include facial data. The images include visible light based images and near-infrared based images. A classifier is trained based on visible light content of the images. The classifier can be modified based on near-infrared content. The classifier is deployed for analysis of additional images of the vehicle occupant. The additional images are analyzed to determine a cognitive state. The vehicle is manipulated based on the cognitive state.

Layers of a deep neural network can include a bottleneck layer 1500. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1510. A feature such as an image feature can include points, edges, objects, boundaries between and among regions, properties, and so on. The deep neural network can include one or more hidden layers 1520. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to an emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1530. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 1540. The number of the hidden layers can include zero hidden layers, one hidden layer, a plurality of hidden layers, and so on. The hidden layers following the bottleneck layer can include more nodes than the bottleneck layer. The deep neural network can include a classification layer 1550. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 16:
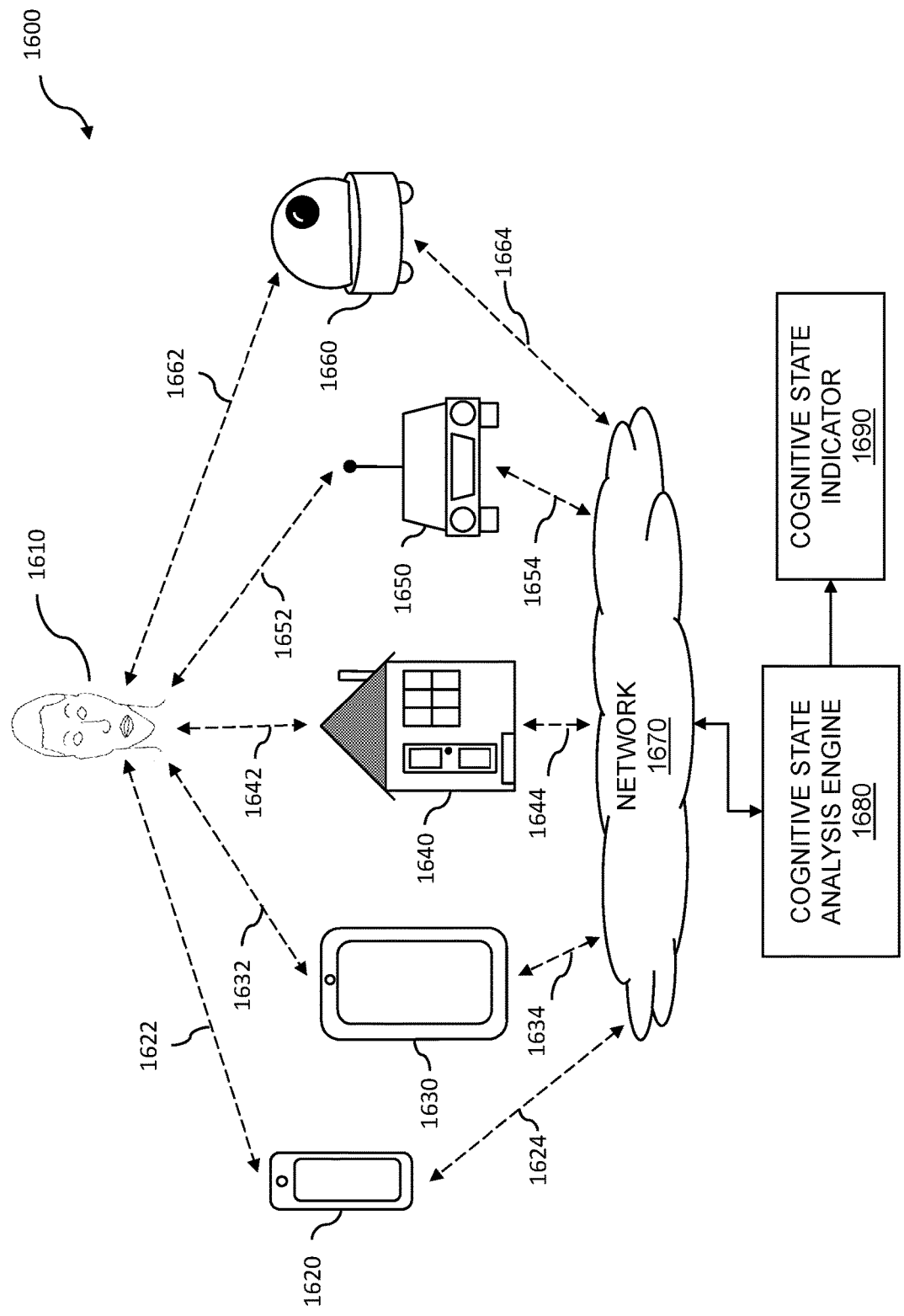
FIG. 16 shows data collection including devices and locations.

FIG. 16 shows data collection including devices and locations 1600. Data, including video data and audio data, can be obtained for vehicle manipulation using image-based analysis. The data can be obtained from multiple devices, vehicles, and locations. Images including facial data of a vehicle occupant are obtained using imaging devices. The images include visible light based images and near-infrared based images. A classifier is trained based on visible light content and can be modified based on near-infrared content. The classifier is deployed for analysis of additional images, where the additional images include near-infrared based images. The additional images are analyzed, and the vehicle is manipulated based on the analysis.

The multiple mobile devices, vehicles, and locations 1600 can be used separately or in combination to collect video data on a user 1610. The video data can include facial data. Other data such as audio data, physiological data, and so on, can be collected on the user. While one person is shown, the video data or other data can be collected on multiple people. A user 1610 can be observed as she or he is performing a task, experiencing an event, viewing a media presentation, and so on. The user 1610 can be shown one or more media presentations, political presentations, social media, or another form of displayed media. The one or more media presentations can be shown to a plurality of people. The media presentations can be displayed on an electronic display coupled to a client device. The data collected on the user 1610 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1610 can be analyzed and viewed for a variety of purposes including expression analysis, mental state analysis, cognitive state analysis, and so on. The electronic display can be on a smartphone 1620 as shown, a tablet computer 1630, a personal digital assistant, a television, a mobile monitor, or any other type of electronic device. In one embodiment, expression data is collected on a mobile device such as a cell phone 1620, a tablet computer 1630, a laptop computer, or a watch. Thus, the multiple sources can include at least one mobile device, such as a phone 1620 or a tablet 1630, or a wearable device such as a watch or glasses (not shown). A mobile device can include a front-facing camera and/or a rear-facing camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1610, data can be collected in a house 1640 using a web camera or the like; in a vehicle 1650 using a web camera, client device, etc.; by a social robot 1660, and so on.

As the user 1610 is monitored, the user 1610 might move due to the nature of the task, boredom, discomfort, distractions, or for another reason. As the user moves, the camera with a view of the user's face can be changed. Thus, as an example, if the user 1610 is looking in a first direction, the line of sight 1622 from the smartphone 1620 is able to observe the user's face, but if the user is looking in a second direction, the line of sight 1632 from the tablet 1630 is able to observe the user's face. Furthermore, in other embodiments, if the user is looking in a third direction, the line of sight 1642 from a camera in the house 1640 is able to observe the user's face, and if the user is looking in a fourth direction, the line of sight 1652 from the camera in the vehicle 1650 is able to observe the user's face. If the user is looking in a fifth direction, the line of sight 1662 from the social robot 1660 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1610 can also use a wearable device including a camera for gathering contextual information and/or collecting expression data on other users. Because the user 1610 can move her or his head, the facial data can be collected intermittently when she or he is looking in a direction of a camera. In some cases, multiple people can be included in the view from one or more cameras, and some embodiments include filtering out faces of one or more other people to determine whether the user 1610 is looking toward a camera. All or some of the expression data can be continuously or sporadically available from the various devices and other devices.

The captured video data can include cognitive content, such as facial expressions, etc., and can be transferred over a network 1670. The network can include the Internet or other computer network. The smartphone 1620 can share video using a link 1624, the tablet 1630 using a link 1634, the house 1640 using a link 1644, the vehicle 1650 using a link 1654, and the social robot 1660 using a link 1664. The links 1624, 1634, 1644, 1654, and 1664 can be wired, wireless, and hybrid links. The captured video data, including facial expressions, can be analyzed on a cognitive state analysis engine 1680, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 1690. The cognitive state indicator 1690 can indicate cognitive states, mental states, moods, emotions, etc. In embodiments, the cognitive state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 17:
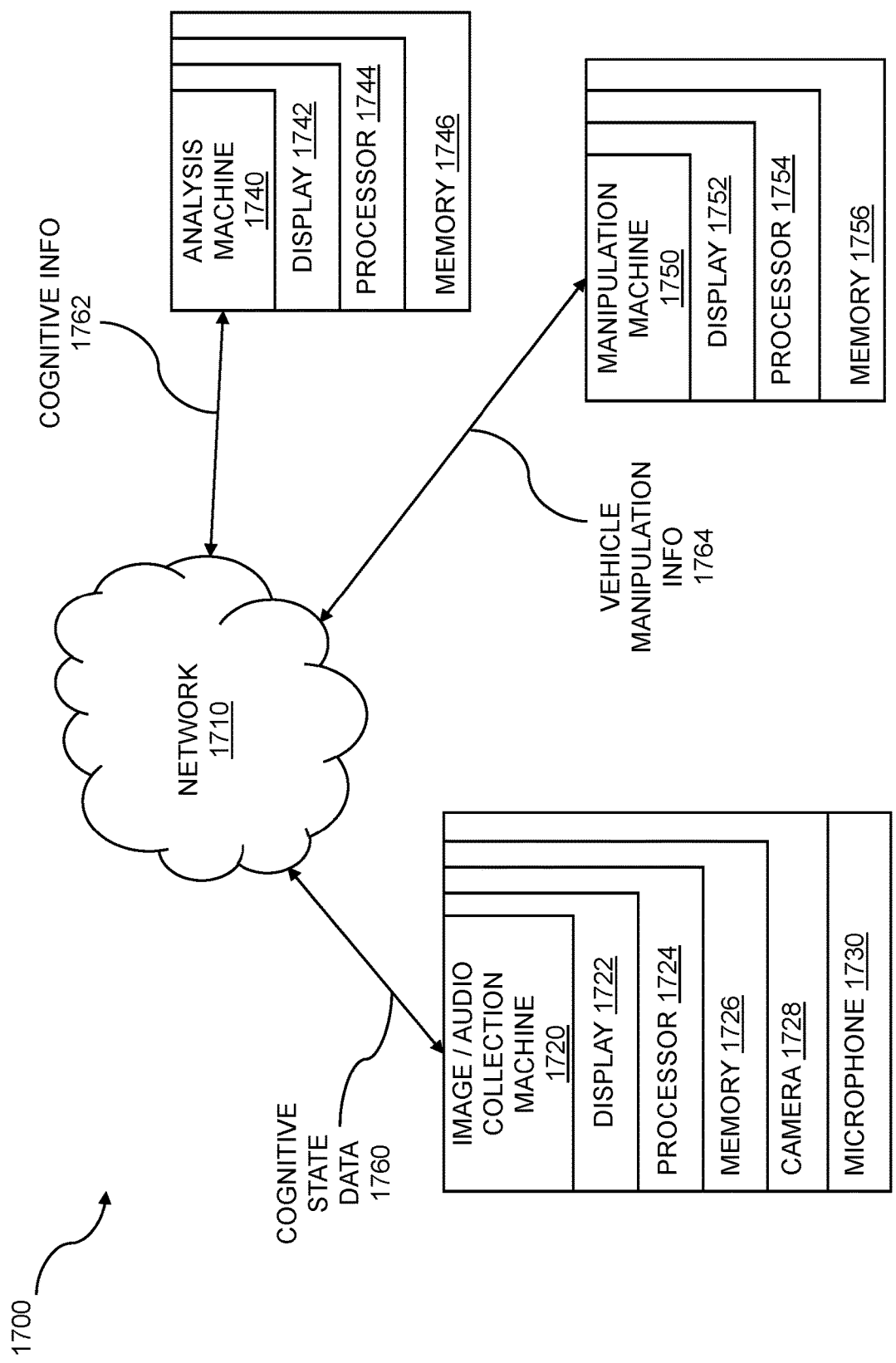
FIG. 17 is a diagram of a system for cognitive state based vehicle manipulation.

FIG. 17 is a diagram of a system 1700 for cognitive state based vehicle manipulation. Cognitive state based vehicle manipulation uses image-based analysis. Images of a vehicle occupant are obtained using imaging devices within the vehicle. The images comprise occupant facial data and include both light-based images and near-infrared images. A classifier is trained based on visible light content of the images. The classifier is modified based on near-infrared content of the images. In embodiments, a classifier can be trained based on visible light content and near-infrared content. The classifier is deployed for analysis of additional images of a vehicle occupant. The additional images can include near-infrared based images. The additional images are analyzed to determine a cognitive state. The vehicle is manipulated based on the cognitive state. The manipulation can include vehicle navigation. In embodiments, the cognitive state can be rendered on a display located within the vehicle.

The network 1710, Internet, intranet, or another computer network, can be used for communication among various machines. An image and audio collection machine 1720 has a memory 1726 which stores instructions and one or more processors 1724 attached to the memory 1726, wherein the one or more processors 1724 can execute instructions. The image and audio collection machine 1720 can also have a network connection to carry cognitive state data 1760, and a display 1722 that can present cognitive state data, cognitive state profiles, mental state data, mental state profiles, emotional states, emotional state profiles, and so on. The image and audio collection machine 1720 can collect cognitive state data including image data, facial data, voice data, audio data, etc., from an occupant of a vehicle. In some embodiments, there are multiple image and audio collection machines 1720 that each collect cognitive state data including facial data. This type of collection machine can have a camera 1728 and/or a microphone 1730. In many embodiments, both a camera and a microphone will be present. Further embodiments include obtaining audio information and augmenting the analyzing of the cognitive state data with the audio information. Once the cognitive state data 1760 has been collected, the image and audio collection machine 1720 can upload information to an analysis machine 1740, based on the cognitive state data from the occupant of the vehicle. The image and audio collection machine 1720 can communicate with the analysis machine 1740 over the network 1710, the Internet, some other computer network, or by another method suitable for communication between two machines. In some embodiments, the analysis machine 1740 functionality is embodied in the image and audio collection machine 1720.

The analysis machine 1740 can have a network connection for cognitive states or cognitive state information 1762, a memory 1746 which stores instructions, and one or more processors 1744 attached to the memory 1746, wherein the one or more processors 1744 can execute instructions. The analysis machine 1740 can receive cognitive state information, collected from an occupant of the vehicle, from the image and audio collection machine 1720, and can learn a cognitive state profile for the occupant. The analysis machine 1740 can also compare further cognitive state data with the cognitive state profile while the occupant is in a second vehicle. In some embodiments, the analysis machine 1740 also has a display 1742 which allows a user to view and evaluate the cognitive state data and cognitive state profiles for the occupant of the vehicle. The analysis machine 1740 can then provide the cognitive state information 1762, which can include a cognitive state profile, to the manipulation machine 1750. In some embodiments, the image and audio collection, or capture, machine 1720 can also function as the manipulation machine 1750. In further embodiments, the cognitive state data that was analyzed can be based on intermittent obtaining of images that include facial data.

The manipulation machine 1750 can have a memory 1756 which stores instructions, and one or more processors 1754 attached to the memory 1756, wherein the one or more processors 1754 can execute instructions. The manipulation machine can use a computer network, the Internet, or another computer communication method, to request the cognitive state information 1762 from the analysis machine. The manipulation machine 1750 can receive vehicle manipulation information 1764, based on the cognitive state data 1760, from the occupant of the vehicle. The cognitive state information and vehicle manipulation information for the occupant can be presented on a display 1752. In some embodiments, the manipulation machine is set up to receive cognitive state data collected from an occupant of the vehicle, in a real-time or near real-time embodiment. In other embodiments, the manipulation machine is set up to receive the cognitive state data on an intermittent basis. In at least one embodiment, a single computer incorporates the image and audio collection machine, the analysis machine, and the manipulation machine functionalities.

In embodiments, a computer program product is embodied in a non-transitory computer readable medium for image-based analysis, the computer program product comprising code which causes one or more processors to perform operations of: obtaining a plurality of images of a vehicle occupant using one or more imaging devices within a vehicle, wherein the plurality of images includes facial data of the vehicle occupant and wherein the plurality of images includes visible light-based images and near-infrared based images; training, using a first computing device, a classifier, based on the visible light content of the one or more images to determine cognitive state data for the vehicle occupant; modifying the classifier based on near-infrared content from the plurality of images; deploying, on a second computing device, the classifier that was modified, for analysis of a plurality of additional images of a vehicle occupant that is obtained, wherein the plurality of additional images comprises near-infrared based images; analyzing, using the second computing device, the plurality of additional images to determine a cognitive state; and manipulating the vehicle, based on the cognitive state that was analyzed.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples but is to be understood in the broadest sense allowable by law.

What is claimed is:

1. A computer-implemented method for image-based analysis comprising:
    obtaining a plurality of images of a vehicle occupant using one or more imaging devices within a vehicle, wherein the plurality of images includes facial data of the vehicle occupant and wherein the plurality of images includes visible light-based images and near-infrared based images;
    training, using a first computing device, a classifier, based on visible light content of the plurality of images to determine cognitive state data for the vehicle occupant;
    modifying the classifier based on near-infrared content from the plurality of images;
    deploying, on a second computing device, the classifier that was modified, for analysis of a plurality of additional images of a vehicle occupant that is obtained, wherein the plurality of additional images comprises near-infrared based images;
    analyzing, using the second computing device, the plurality of additional images to determine a cognitive state; and
    manipulating the vehicle, based on the cognitive state that was analyzed.

2. The method of claim 1 further comprising rendering the cognitive state on a display located within the vehicle.

3. The method of claim 1 further comprising transmitting the cognitive state to a third computing device, wherein the third computing device is external to the vehicle.

4. The method of claim 1 further comprising obtaining further additional images of one or more additional occupants of the vehicle, wherein the further additional images comprise near-infrared based images.

5. The method of claim 4 further comprising generating a combined cognitive metric for the vehicle occupant and the one or more additional occupants.

6. The method of claim 1 wherein a wavelength of the near infrared light is less than 950 nm.

7. The method of claim 1 wherein the vehicle occupant is a driver of the vehicle.

8. The method of claim 1 further comprising obtaining yet further additional images of one or more additional occupants of one or more additional vehicles, wherein the yet further additional images comprise near-infrared based images.

9. The method of claim 8 wherein the yet further additional images are used to determine aggregated cognitive state data for one or more segments of a vehicle travel route.

10. The method of claim 9 wherein the aggregated cognitive state data for one or more segments of the vehicle travel route comprise a vehicle route mood map.

11. The method of claim 1 further comprising obtaining audio information from the vehicle occupant and augmenting the analyzing based on the audio information.

12. The method of claim 11 wherein the audio information includes speech.

13. The method of claim 11 wherein the audio information includes non-speech vocalizations.

14. The method of claim 13 wherein the non-speech vocalizations include grunts, yelps, squeals, snoring, sighs, laughter, filled pauses, unfilled pauses, or yawns.

15. The method of claim 1 further comprising obtaining one or more further additional images of the vehicle occupant using a second imaging device.

16. The method of claim 1 further comprising obtaining one or more further additional images of one or more additional vehicle occupants using the one or more imaging devices.

17. The method of claim 1 further comprising obtaining one or more further additional images of one or more additional vehicle occupants using at least a second imaging device.

18. The method of claim 1 wherein the plurality of images is used to perform facial recognition.

19. The method of claim 18 wherein the facial recognition is used to generate vehicle seating maps.

20. The method of claim 1 wherein the analyzing is performed using deep learning.

21. The method of claim 1 further comprising tagging the cognitive state data with sensor data.

22. The method of claim 21 wherein the sensor data includes one or more of vehicle temperature, outside temperature, time of day, level of daylight, weather conditions, headlight activation, windshield wiper activation, entertainment center selection, or entertainment center volume.

23. The method of claim 1 wherein the cognitive state includes drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

24. The method of claim 1 wherein the cognitive state data that was analyzed is based on intermittent obtaining of images that include facial data.

25. A computer program product embodied in a non-transitory computer readable medium for image-based analysis, the computer program product comprising code which causes one or more processors to perform operations of:
obtaining a plurality of images of a vehicle occupant using one or more imaging devices within a vehicle, wherein the plurality of images includes facial data of the vehicle occupant and wherein the plurality of images includes visible light-based images and near-infrared based images;
training, using a first computing device, a classifier, based on visible light content of the plurality of images to determine cognitive state data for the vehicle occupant;
modifying the classifier based on near-infrared content from the plurality of images;
deploying, on a second computing device, the classifier that was modified, for analysis of a plurality of additional images of a vehicle occupant that is obtained, wherein the plurality of additional images comprises near-infrared based images;
analyzing, using the second computing device, the plurality of additional images to determine a cognitive state; and
manipulating the vehicle, based on the cognitive state that was analyzed.

26. A computer system for image-based analysis comprising:
a memory which stores instructions;
one or more processors attached to the memory wherein the one or more processors, when executing the instructions which are stored, are configured to:
obtain a plurality of images of a vehicle occupant using one or more imaging devices within a vehicle, wherein the plurality of images includes facial data of the vehicle occupant and wherein the plurality of images includes visible light-based images and near-infrared based images;
train, using a first computing device, a classifier, based on visible light content of the plurality of images to determine cognitive state data for the vehicle occupant;
modify the classifier based on near-infrared content from the plurality of images;
deploy, on a second computing device, the classifier that was modified, for analysis of a plurality of additional images of a vehicle occupant that is obtained, wherein the plurality of additional images comprises near-infrared based images;
analyze, using the second computing device, the plurality of additional images to determine a cognitive state; and
manipulate the vehicle, based on the cognitive state that was analyzed.

* * * * *